United States Patent
Lee et al.

(10) Patent No.: US 9,469,606 B2
(45) Date of Patent: Oct. 18, 2016

(54) WNT/β-CATENIN INHIBITORS AND METHODS OF USE

(71) Applicant: The General Hospital Corporation, Boston, MA (US)

(72) Inventors: Sam W. Lee, Newton Center, MA (US); Anna I. Mandinova, Newton, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 14/353,667

(22) PCT Filed: Oct. 25, 2012

(86) PCT No.: PCT/US2012/061992
§ 371 (c)(1),
(2) Date: Apr. 23, 2014

(87) PCT Pub. No.: WO2013/063321
PCT Pub. Date: May 2, 2013

(65) Prior Publication Data
US 2014/0288174 A1     Sep. 25, 2014

Related U.S. Application Data

(60) Provisional application No. 61/551,099, filed on Oct. 25, 2011.

(51) Int. Cl.
*C07C 317/48*     (2006.01)
*C07C 317/32*     (2006.01)
*A61K 31/18*      (2006.01)

(52) U.S. Cl.
CPC .............. *C07C 317/48* (2013.01); *A61K 31/18* (2013.01); *C07C 317/32* (2013.01)

(58) Field of Classification Search
CPC ........................... C07C 317/48; C07C 317/32
USPC .................................................. 514/535, 604
See application file for complete search history.

(56) References Cited

U.S. PATENT DOCUMENTS

| | | | |
|---|---|---|---|
| 5,559,150 A | 9/1996 | Soll | |
| 5,741,819 A * | 4/1998 | Illig | C07C 311/21 514/305 |
| 2008/0146548 A1 | 6/2008 | Potter et al. | |
| 2009/0176776 A1 | 7/2009 | Prevelige | |

FOREIGN PATENT DOCUMENTS

| | | |
|---|---|---|
| CN | 101817767 | 1/2010 |
| CN | 101817767 | 9/2010 |
| WO | WO 01/53268 | 7/2001 |
| WO | WO 2005/009997 | 2/2005 |
| WO | 2007/071443 | 6/2007 |
| WO | WO 2007/071443 | 6/2007 |
| WO | 2008/076918 | 6/2008 |
| WO | WO 2008/071398 | * 6/2008 |
| WO | WO 2008/076918 | 6/2008 |
| WO | 2009/106361 | 9/2009 |
| WO | WO 2009/106361 | 9/2009 |

OTHER PUBLICATIONS

Perusini (Masters Thesis (2008).*
Wei et al. Molecular Cancer 2009, 8:76.*
Chen et al. Cancer 2004;101:1345-56.*
Akiri et al., "Wnt pathway aberrations including autocrine Wnt activation occur at high frequency in human non-small-cell lung carcinoma," Oncogene, May 28, 2009, 28(21):2163-72.
Bafico et al., "An autocrine mechanism for constitutive Wnt pathway activation in human cancer cells," Cancer Cell. Nov. 2004, 6(5): 497-506.
Bafico et al., "Characterization of Wnt-1 and Wnt-2 induced growth alterations and signaling pathways in NIH3T3 fibroblasts," Oncogene May 28, 1998, 16(21):2819-25.
Barker and Clevers, "Mining the Wnt pathway for cancer therapeutics," Nat Rev Drug Discov., Dec. 2006, 5(12):997-1014.
Bialkowska and Yang, "High-throughput screening strategies for targeted identification of therapeutic compounds in colorectal cancer," Future Oncol. Mar. 2012, 8(3):259-72.
Chen et al., "Small molecule-mediated disruption of Wnt-dependent signaling in tissue regeneration and cancer," Nat Chem Biol. Feb. 2009, 5(2): 100-7.
Chen et al., "The β-catenin/TCF complex as a novel target of resveratrol in the Wnt/β-catenin signaling pathway," Biochem Pharmacol Nov. 1, 2012, 84(9): 1143-53.
Clevers and Nusse, "Wnt/β-catenin signaling and disease," Cell, Jun. 8, 2012, 149(6):1192-205.
Ewan et al., "A useful approach to identify novel small-molecule inhibitors of Wnt-dependent transcription," Cancer Res. Jul. 15, 2010 70(14): 5963-73.
Grossmann et al., "Inhibition of oncogenic Wnt signaling through direct targeting of β-catenin," Proc Natl Acad Sci USA, Oct. 30, 2012, 109(44):17942-7.
Huang et al., "Changes in gene expression during the development of mammary tumors in MMTV-Wnt-1 transgenic mice," Genome Biol., Sep. 30, 2005, 6(10):R84.
Huang et al., "Tankyrase inhibition stabilizes axin and antagonizes Wnt signalling," Nature, Oct. 1, 2009, 461(7264):614-20.
International Preliminary Report on Patentability in International Application No. PCT/US2012/061992, mailed on May 8, 2014, 3 pages.
International Search Report in International Application No. PCT/US2012/061992, mailed on Feb. 14, 2013, 3 pages.
(Continued)

*Primary Examiner* — Shirley V Gembeh
(74) *Attorney, Agent, or Firm* — Fish & Richardson P.C.

(57) ABSTRACT

This disclosure relates to inhibitors of the Wni pathway, and compositions comprising the same, as well as to their use in the treatment of disorders characterized by the activation of Writ pathway signaling (e.g., cancer), as well as to the modulation of cellular events mediated by VVnt pathway signaling.

9 Claims, 30 Drawing Sheets

(56) References Cited

OTHER PUBLICATIONS

Lepourcelet et al., "Small-molecule antagonists of the oncogenic Tcf/beta-catenin protein complex," Cancer Cell, Jan. 2004, 5(1):91-102.

Liu et al., "Androgen-induced Wnt signaling in preosteoblasts promotes the growth of MDA-PCa-2b human prostate cancer cells," Cancer Res, Jun. 15, 2007, 67(12):5747-53.

Polakis, "Drugging Wnt signalling in cancer," Embo. J., May 22, 2012, 31(12):2737-46.

Raj et al., "Selective killing of cancer cells by a small molecule targeting the stress response to ROS," Nature, Jul. 13, 2011, 475(7355):231-4.

Song et al., "Wnt inhibitor screen reveals iron dependence of β-catenin signaling in cancers," Cancer Res., Dec. 15, 2011, 71(24):7628-39.

Thorne et al., "Small-molecule inhibition of Wnt signaling through activation of casein kinase 1α," Nat Chem Biol., Nov. 2010, 6(11):829-36.

Wei et al., "Small molecule antagonists of Tcf4/beta-catenin complex inhibit the growth of HCC cells in vitro and in vivo," Int J Cancer, May 15, 2010, 126(10):2426-36.

Xie et al, "Inhibition of Tcf-4 induces apoptosis and enhances chemosensitivity of colon cancer cells," PLoS One, Sep. 24, 2012, 7(9):e45617.

International Search Report and Written Opinion mailed Feb. 14, 2013, in International Application No. PCT/US2012/061992, 7 pgs.

* cited by examiner

OC0021 methyl 3-{[(4-methylphenyl)sulfonyl]amino}benzoate

Hit Selection ; Inhibit the TCF/LEF reporter >50% (as compared to DMSO control), CV < 12%

→ Confirmed the inhibition efficiency observed from HTS assay

W100: Wnt3a recombinant 100ng/ml
W200: Wnt3a recombinant 200ng/ml

PV: pyrvinium pamoate,
A known Wnt/β-catenin inhibitor

→ Compound OC0021 increased β-catenin phosphorylation (T41/S45), indicating that it promotes the phosphorylation-dependent degradation of β-catenin.

→ Compound #21 downregulates the protein level of endogenous β-catenin/ TCF-dependent genes, Cyclin D1 and c-Myc, and enhances stability of axin1 and axin2.

→ Compound 0021 decreased β-catenin binding to its target gene promoters.

→ Cell viability inhibition effect of Compound #21 was highly specific to Wnt-dependent cell lines.

*In vivo*, OC0021 did not inhibit cell growth of Wnt-independent lung cancer cell, H460

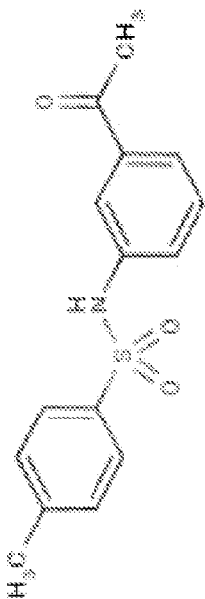
15A
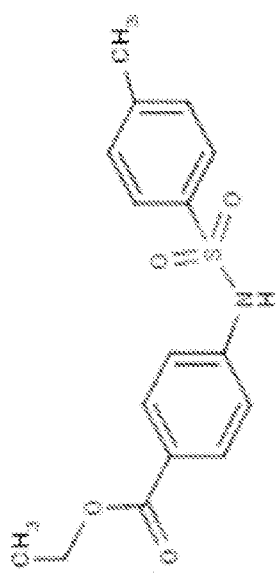
17A
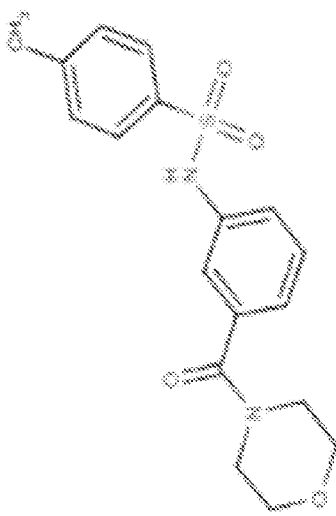
19A
FIG. 17C
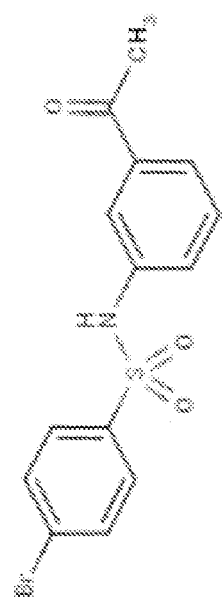
14A
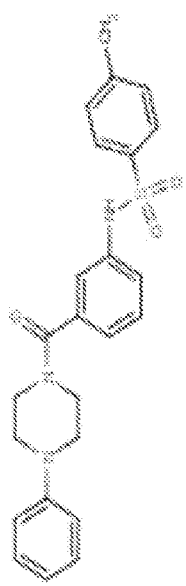
16A
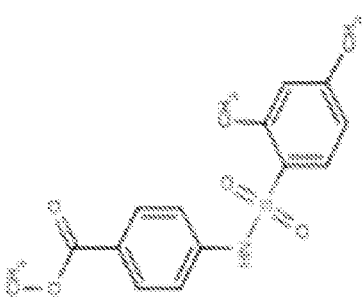
18A

33A

35A

37A

36A

WNT/B-CATENIN INHIBITORS AND METHODS OF USE

CROSS-REFERENCE TO RELATED APPLICATIONS

This application is a U.S. National Phase Application under 35 U.S.C. §371 of International Patent Application No. PCT/US2012/061992, filed on Oct. 25, 2012, which claims priority to U.S. Provisional Application Ser. No. 61/561,099, filed on Oct. 25, 2011, the entire contents of the foregoing are hereby incorporated by reference.

TECHNICAL FIELD

This disclosure relates to inhibitors of one or more proteins in the Wnt pathway, including inhibitors of one or more Wnt proteins, and compositions comprising the same. This disclosure also relates to the use of such inhibitors in the treatment of disorders characterized by the activation of Wnt pathway signaling (e.g., cancer, abnormal cellular proliferation, angiogenesis), as well as to the modulation of cellular events mediated by Wnt pathway signaling.

BACKGROUND

The canonical Wnt signaling pathway may be the most relevant of the Wnt signaling pathways to the development of cancer. Normal activation of this pathway begins a series of downstream events culminating in the stabilization and increased levels of the protein β-catenin. This protein is normally an inactive cytoplasmic protein, and is found at the cell membrane bound to proteins including E-cadherin. In the absence of Wnt ligand, phosphorylated cytoplasmic β-catenin is normally rapidly degraded. Upon activation of the canonical pathway, unphosphorylated β-catenin is transported to the nucleus where it further results in transcriptional activation of various target genes. The subsequent upregulation in transcription of these target genes leads to changes in the cell, and continuous, unregulated expression of such target genes results in tumor development. Since aberrant Wnt signaling appears to be a necessary precursor in carcinogenesis, effective inhibitors of Wnt signaling are of great interest as cancer therapeutics.

SUMMARY

The compounds and compositions described herein can be used as anti-proliferative agents, e.g., anti-cancer and anti-angiogenesis agents, and as inhibitors of the Wnt signaling pathway, e.g., for treating diseases or disorders associated with aberrant Wnt signaling. Such compounds and compositions are also useful for controlling cellular proliferation, differentiation, and/or apoptosis.

Provided herein is a method of treating cancer in a patient, the method comprising administering to the patient a therapeutically effective amount of a compound selected from the group consisting of:

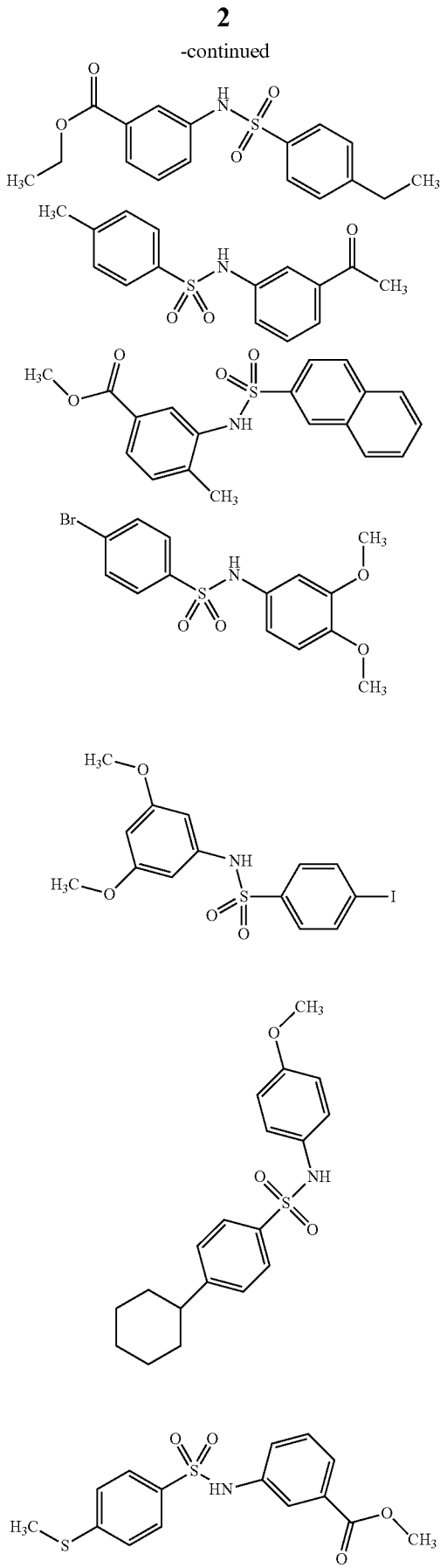

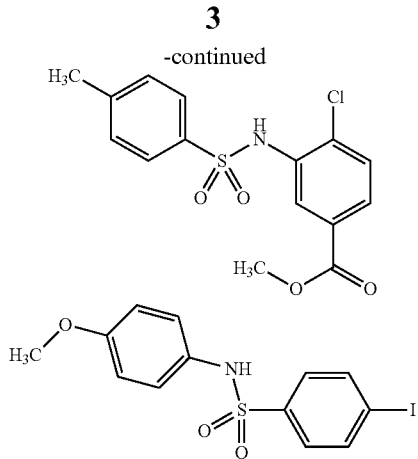

or a pharmaceutically acceptable salt thereof.

In some embodiments, the compound is:

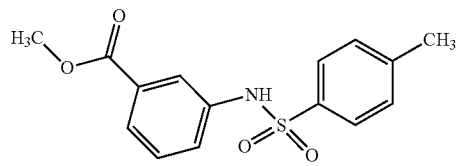

or a pharmaceutically acceptable salt thereof.

In some embodiments, the patient is a human.

The cancer can be selected from the group consisting of: colorectal cancer, gastric carcinoma, heptaocellulcar carcinoma, fibromatosis, melanoma, medulloblastoma, and prostate cancer. For example, the cancer can be a Wnt-dependent cancer.

The compounds provided herein can be effective to inhibit one or more proteins in the Wnt pathway. For example, the compound can inhibit one or more Wnt proteins. Non-limiting examples of Wnt proteins include: WNT1, WNT2, WNT2B, WNT3, WNT3A, WNT4. WNT5A, WNT5B, WNT6, WNT7A, WNT7B, WNT8A, WNT8B, WNT9A, WNT9B, WNT10A, WNT10B, WNT11, and WNT16.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION

Figure 1:
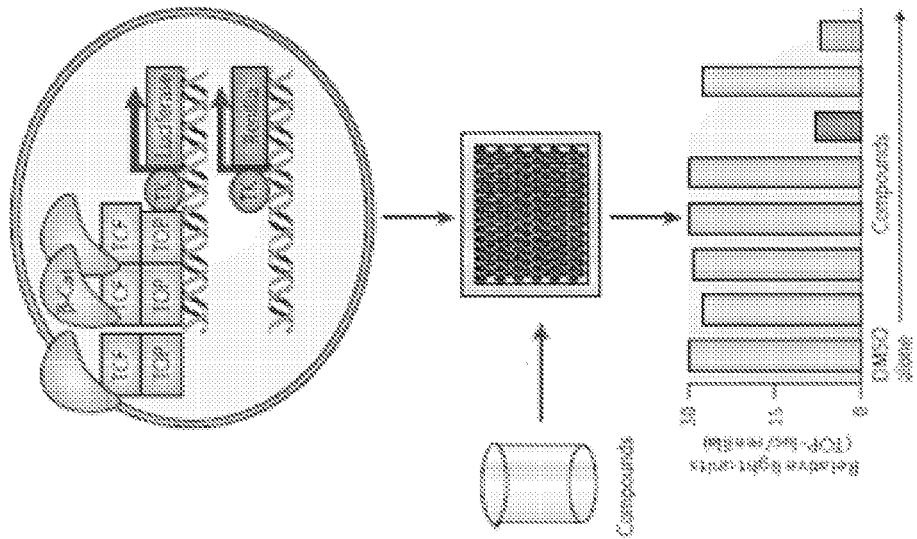
FIG. 1 shows an overview of the High-Throughput-Screening Strategy for Wnt/beta-catenin inhibitors using Wnt-dependent HCT116 containing TOP-Luciferase.
Figure 1:
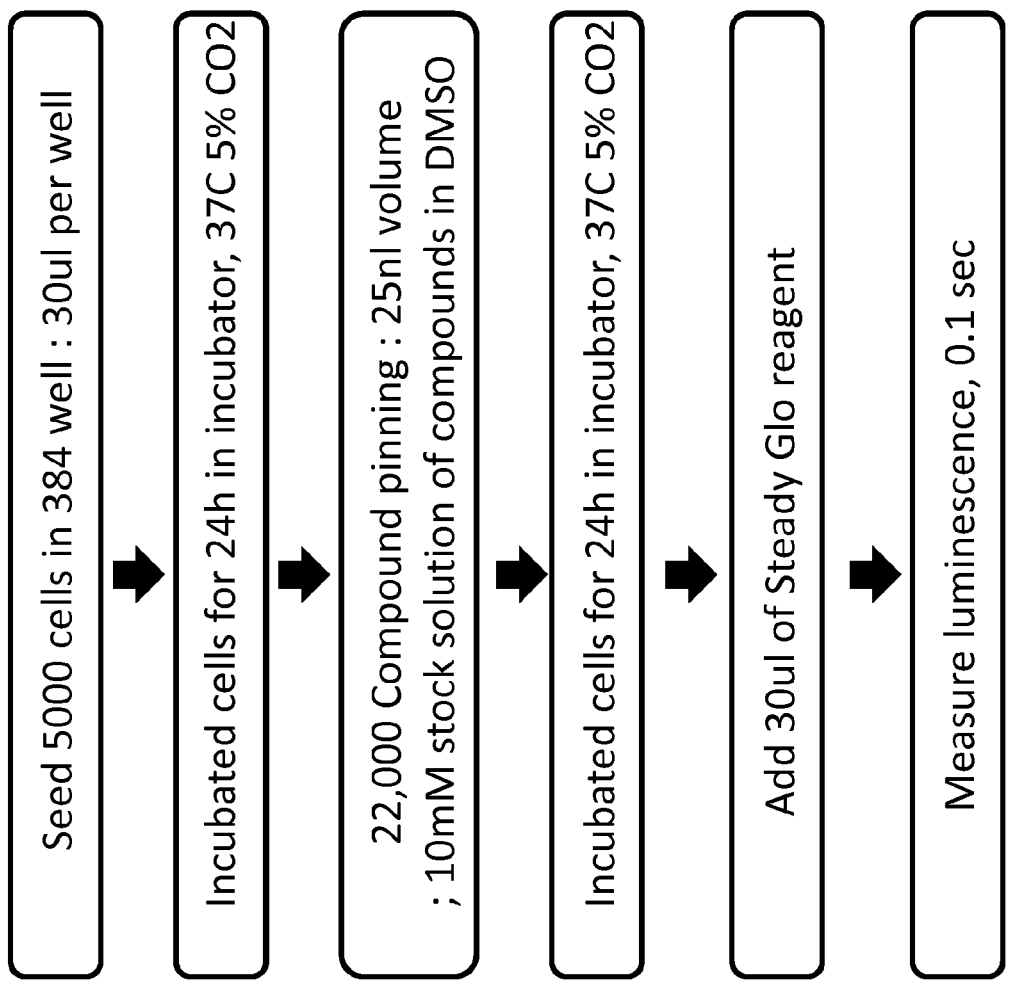

The compounds and compositions described herein can be used as anti-proliferative agents, e.g., anti-cancer and anti-angiogenesis agents, and as inhibitors of the Wnt signaling pathway, e.g., for treating diseases or disorders associated with aberrant Wnt signaling. Such compounds and compositions are also useful for controlling cellular proliferation, differentiation, and/or apoptosis.

A. DEFINITIONS

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

As used herein, the singular forms "a," "an," and "the" include plural referents unless the context clearly dictates otherwise.

A "patient", as used herein, includes both humans and other animals, particularly mammals. Thus the methods are applicable to both human therapy and veterinary applications. In some embodiments, the patient is a mammal, for example, a primate. In some embodiments, the patient is a human.

The terms "treating" and "treatment" mean causing a therapeutically beneficial effect, such as ameliorating existing symptoms, preventing additional symptoms, ameliorating or preventing the underlying metabolic causes of symptoms, postponing or preventing the further development of a disorder and/or reducing the severity of symptoms that will or are expected to develop.

A "therapeutically effective" amount of the compounds described herein is typically one which is sufficient to achieve the desired effect and may vary according to the nature and severity of the disease condition, and the potency of the compound. It will be appreciated that different concentrations may be employed for prophylaxis than for treatment of an active disease.

The term "contacting" means bringing at least two moieties together, whether in an in vitro system or an in vivo system.

As used herein, "administration" refers to delivery of a compound or composition as described herein by any external route, including, without limitation, IV, intramuscular, SC, intranasal, inhalation, transdermal, oral, buccal, rectal, sublingual, and parenteral administration.

The compounds provided herein may encompass various stereochemical forms and tautomers. The compounds also encompasses diastereomers as well as optical isomers, e.g. mixtures of enantiomers including racemic mixtures, as well as individual enantiomers and diastereomers, which arise as a consequence of structural asymmetry in certain compounds. Separation of the individual isomers or selective synthesis of the individual isomers is accomplished by application of various methods which are well known to practitioners in the art.

B. COMPOUNDS

The compounds and compositions described herein can be used as anti-proliferative agents, e.g., anti-cancer and anti-angiogenesis agents, and as inhibitors of the Wnt signaling pathway, e.g., for treating diseases or disorders associated with aberrant Wnt signaling. Such compounds and compositions are also useful for controlling cellular proliferation, differentiation, and/or apoptosis.

A compound, as provided herein, can be selected from the group consisting of:

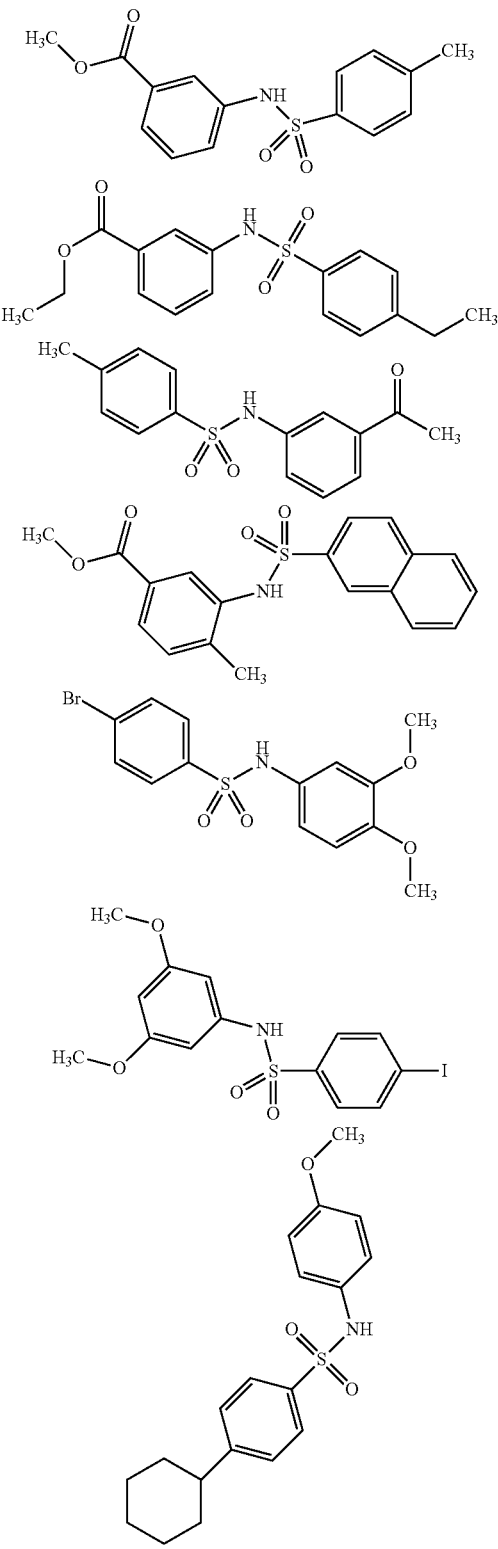

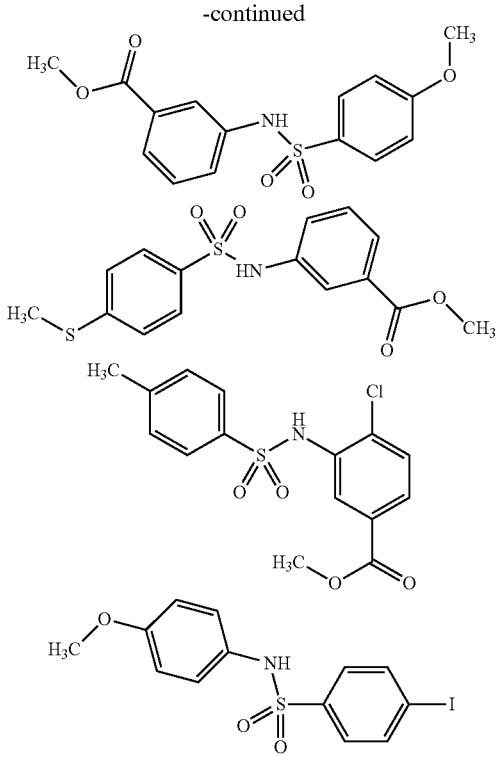

or a pharmaceutically acceptable salt thereof.

Pharmaceutically acceptable salts of the compounds described herein include the acid addition and base salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, hydrogen phosphate, isethionate, D- and L-lactate, malate, maleate, malonate, mesylate, methylsulphate, 2-napsylate, nicotinate, nitrate, orotate, oxalate, palmitate, pamoate, phosphate/hydrogen, phosphate/phosphate dihydrogen, pyroglutamate, saccharate, stearate, succinate, tannate, D- and L-tartrate, 1-hydroxy-2-naphthoate tosylate and xinafoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

A person skilled in the art will know how to prepare and select suitable salt forms for example, as described in "Handbook of Pharmaceutical Salts: Properties, Selection, and Use" by Stahl and Wermuth (Wiley-VCH, Weinheim, Germany, 2002).

The compounds for use in the compositions and methods provided herein may be obtained from commercial sources (e.g., ChemBridge Corporation San Diego, Calif.), may be prepared by methods well known to those of skill in the art, or may be prepared by the methods shown herein. One of skill in the art would be able to prepare all of the compounds for use herein by routine modification of these methods using the appropriate starting materials.

C. PHARMACEUTICAL COMPOSITIONS

Some embodiments include pharmaceutical compositions comprising: (a) a safe and therapeutically effective amount of a compound described herein, or its corresponding enantiomer, diastereoisomer or tautomer, or pharmaceutically acceptable salt; and (b) a pharmaceutically acceptable carrier.

Administration of the compounds disclosed herein or the pharmaceutically acceptable salts thereof can be via any of the accepted modes of administration for agents that serve similar utilities including, but not limited to, orally, subcutaneously, intravenously, intranasally, topically, transdermally, intraperitoneally, intramuscularly, intrapulmonarily, vaginally, rectally, or intraocularly. Oral and parenteral administrations are customary in treating the indications.

The compounds provided herein which are intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

The compounds may be administered alone or in combination with one or more other compounds described herein or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Non-limiting examples of pharmaceutical excipients suitable for administration of the compounds provided herein include any such carriers known to those skilled in the art to be suitable for the particular mode of administration. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-b-cyclodextrins, or other solubilized derivatives can also be advantageously used to enhance delivery of compounds of the formulae described herein. In some embodiments, the excipient is a physiologically acceptable saline solution.

The compositions can be, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers (see, e.g., Ansel Introduction to Pharmaceutical Dosage Forms, Fourth Edition 1985, 126).

The concentration of a compound in a pharmaceutical composition will depend on absorption, inactivation and excretion rates of the compound, the physicochemical characteristics of the compound, the dosage schedule, and amount administered as well as other factors known to those of skill in the art.

The pharmaceutical composition may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. Unit-dose forms as used herein refers to physically discrete units suitable for human and animal patients and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Dosage forms or compositions containing a compound as described herein in the range of 0.005% to 100%0/with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%.

Pharmaceutical compositions suitable for the delivery of compounds described herein and methods for their preparation will be readily apparent to those skilled in the art. Such compositions and methods for their preparation may be found, for example, in "Remington's Pharmaceutical Sciences", 19th Edition (Mack Publishing Company, 1995).

D. METHODS OF USE

The compounds and compositions provided herein can be used as inhibitors of one or more members of the Wnt pathway, including one or more Wnt proteins, and thus can be used to treat a variety of disorders and diseases in which aberrant Wnt signaling is implicated, such as cancer. Accordingly, the compounds and compositions provided herein can be used to treat cancer, to reduce or inhibit angiogenesis, and to reduce or inhibit cellular proliferation.

With respect to cancer, the Wnt pathway is known to be constitutively activated in a variety of cancers including, for example, colorectal cancer (e.g., colon cancer) such as colon cancers having >85% APC mutation, gastric carcinoma (e.g., gastric carcinomas having a >15% β-catenin mutation), hepatocellular carcinoma, fibromatosis, melanoma, medulloblastoma, lung cancer, ovarian cancer, prostate cancer and leukemias such as CML, CLL and T-ALL. The constitutive activation is due to constitutively active β-catenin, perhaps due to its stabilization by interacting factors or inhibition of the degradation pathway. Accordingly, the compounds and compositions described herein may be used to treat cancers in which the Wrt pathway is constitutively activated: the methods can include obtaining a sample comprising cells from a cancer (e.g., tumor cells, e.g., obtained during a biopsy or resection) in a subject, assaying for levels of Wnt activation, and selecting the subject for treatment with (and optionally administering) a compound described herein if aberrant (elevated, constitutive) Wnt signaling is present; methods for assaying for Wnt activity are known in the art. In certain embodiments, the cancer is chosen from colorectal cancer, gastric carcinoma, heptaocellulcar carcinoma, fibromatosis, melanoma, medulloblastoma, and prostate cancer. In some embodiments, the cancer is a Wnt-dependent cancer, e.g., the methods include identifying the cancer as a Wnt-dependent cancer.

Other cancers can also be treated with the compounds and compositions described herein.

More particularly, cancers that may be treated by the compound, compositions and methods described herein include, but are not limited to, the following:

1) Breast cancers, including, for example $ER^+$ breast cancer, $ER^-$ breast cancer, $her2^-$ breast cancer, $her2^+$ breast cancer, stromal tumors such as fibroadenomas, phyllodes tumors, and sarcomas, and epithelial tumors such as large duct papillomas; carcinomas of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma; and miscellaneous malignant neoplasms. Further examples of breast cancers can include luminal A, luminal B, basal A, basal B, and triple negative breast cancer, which is estrogen receptor negative (ER⁻), progesterone receptor negative, and her2 negative (her2⁻). In some embodiments, the breast cancer may have a high risk Oncotype score.

2) Cardiac cancers, including, for example sarcoma, e.g., angiosarcoma, fibrosarcoma, rhabdomyosarcoma, and liposarcoma; myxoma; rhabdomyoma; fibroma; lipoma and teratoma.

3) Lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma.

4) Gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma.

5) Genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma.

6) Liver cancers, including, for example, hepatoma, e.g., hepatocellular carcinoma; cholangiocarcinoma; hepatoblastoma; angiosarcoma; hepatocellular adenoma: and hemangioma.

7) Bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors.

8) Nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma.

9) Gynecological cancers, including, for example, cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, mucinous cystadenocarcinoma, unclassified carcinoma, granulosa thecal cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma.

10) Hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non-Hodgkin's lymphoma (malignant lymphoma) and Waldenström's macroglobulinemia.

11) Skin cancers and skin disorders, including, for example, malignant melanoma, basal cell carcinoma, squamous cell carcinoma, Kaposi's sarcoma, moles dysplastic nevi, lipoma, angioma, dermatofibroma, keloids, and psoriasis.

12) Adrenal gland cancers, including, for example, neuroblastoma.

Cancers may be solid tumors that may or may not be metastatic. Cancers may also occur, as in leukemia, as a diffuse tissue. Thus, the term "tumor cell," as provided herein, includes a cell afflicted by any one of the above identified disorders.

A method of treating cancer using a compound or composition as described herein may be combined with existing methods of treating cancers, for example by chemotherapy, irradiation, or surgery. In some embodiments, a compound or composition can be administered before, during, or after another anticancer agent or treatment.

The compounds and compositions may also be useful in the inhibition of the development of invasive cancer, tumor angiogenesis and metastasis.

The compounds provided herein are effective inhibitors of one or more proteins in the Wnt pathway. A Wnt protein can be, for example, WNT1, WNT2, WNT2B, WNT3, WNT3A, WNT4, WNT5A, WNT5B, WNT6, WNT7A, WNT7B, WNT8A, WNT8B, WNT9A, WNT9B, WNT10A, WNT10B, WNT11, or WNT16. A compound provided herein can decrease TCF promoter activity in a dose-dependent manner, decrease β-catenin recruitment level on target gene promoters: and/or decrease mRNA levels of Wnt target genes such as cyclin D1, c-Myc, Axin-2 or BMP4. In some embodiments, the compounds provided herein can inhibit nuclear translocation of β-catenin; decrease FOXM1 nuclear translocation; enhance phosphorylation of β-catenin protein; and/or induce degradation of β-catenin protein levels. In some embodiments, a compound provided herein is effective to inhibit cell growth of a Wnt-dependent cancer cell. For example, the compound can inhibit cell growth of a Wnt-dependent cancer cell, but show little effect in a Wnt-independent cancer cell.

The changes described above can be effected in a cell by a method comprising contacting the cell with an effective amount of compound provided herein, or a pharmaceutically acceptable salt form thereof. The method may be performed by contacting the cell with a compound provided herein, in vitro or in vivo. Uses of such an in vitro method include, but are not limited to use in a screening assay (for example, wherein the compound is used as a positive control or standard compared to compounds of unknown activity or potency). The in vivo methods described herein can include contacting the cell by causing a compound provided herein to be present in an individual in an effective amount to achieve the desired change (e.g., inhibition of a Wnt protein). This may be achieved, for example, by administering an effective amount of the compound, or a pharmaceutically acceptable salt form thereof, to the individual. Uses of such an in vivo method include, but are not limited to, use in methods of treating a disease or condition, wherein the desired change is beneficial.

Evaluation of Biological Activity

The biological activity of the compounds described herein can be tested using any suitable assay known to those of skill in the art, e.g., WO 2001/053268 or WO 2005/009997. For example, the activity of a compound may be tested using one or more of the test methods outlined below.

Figure 17A:
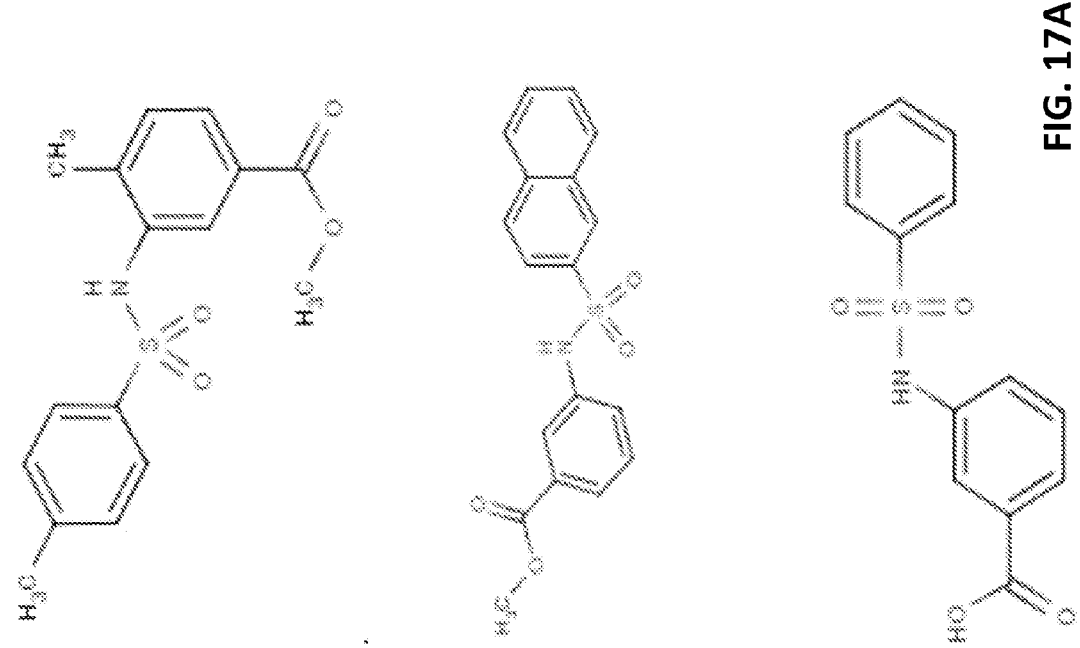
FIG. 17 shows the compounds which were classified as ineffective based on the results of the screening assay.
Figure 17A:
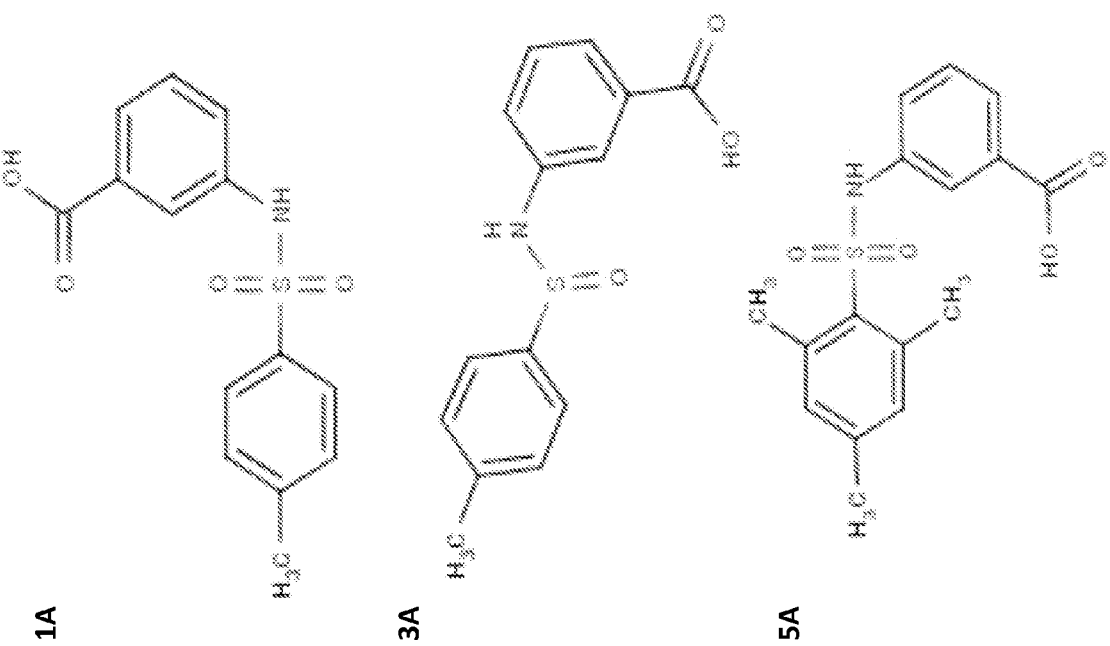
Figure 17B:
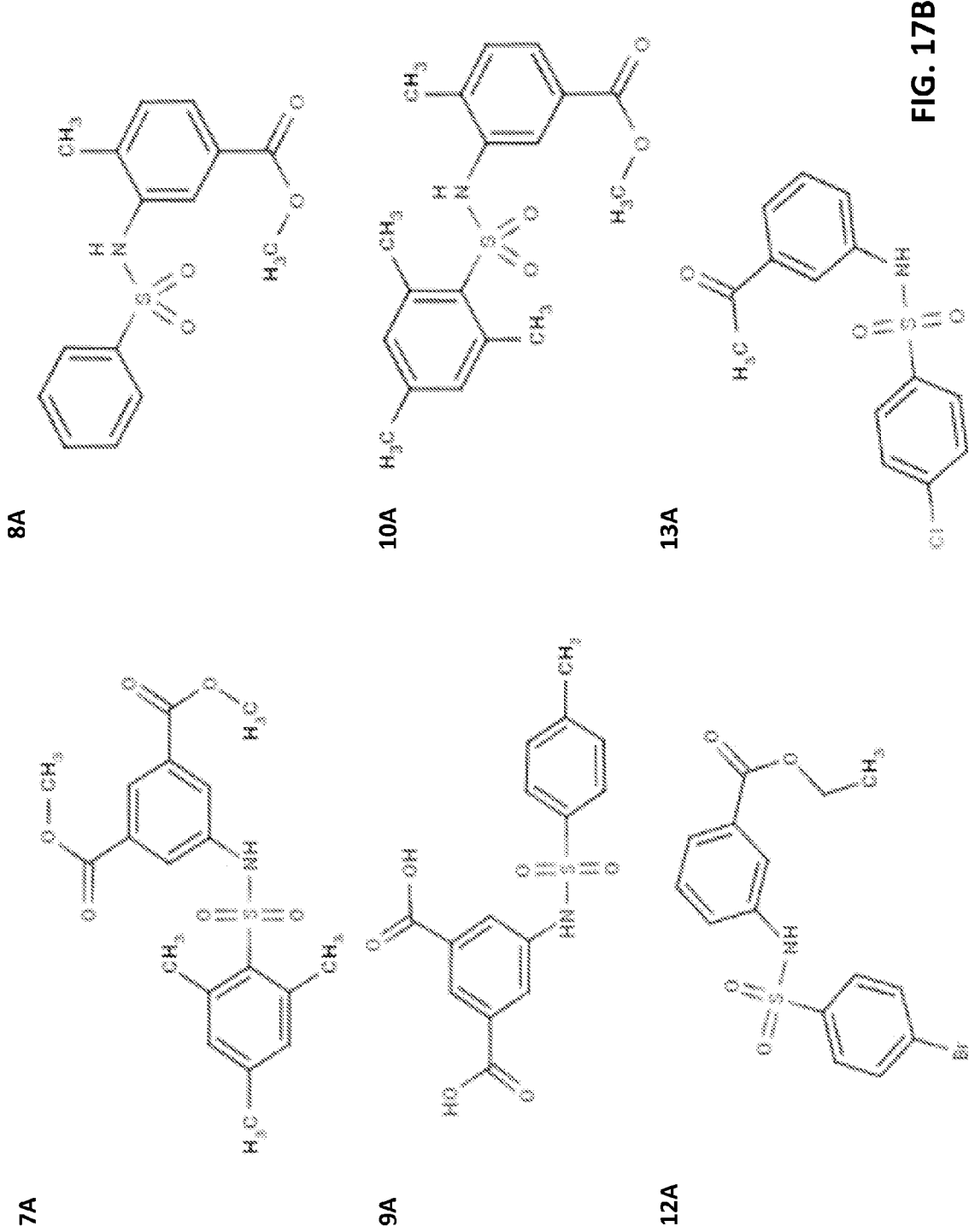
Figure 17D:
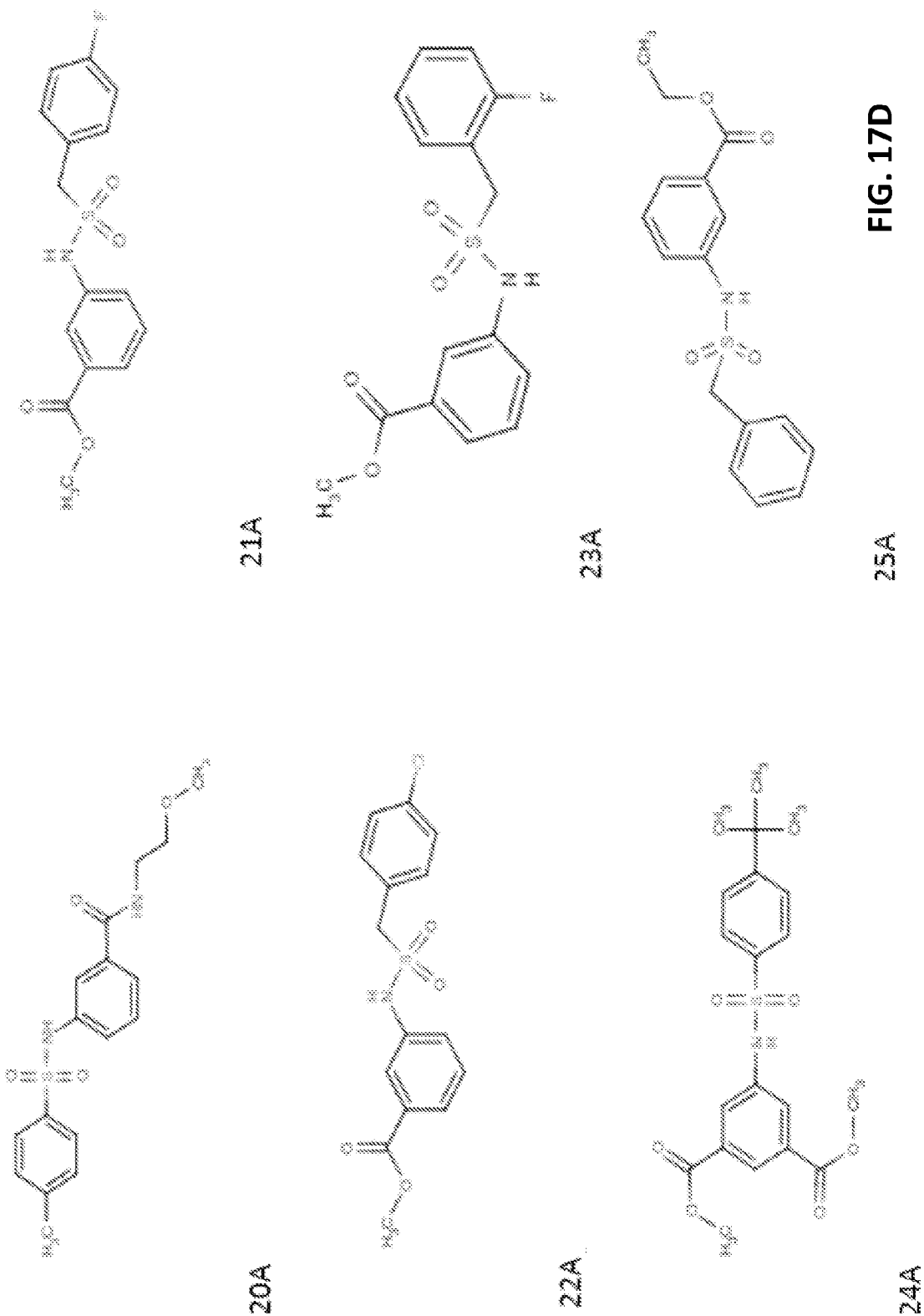
Figure 17E:
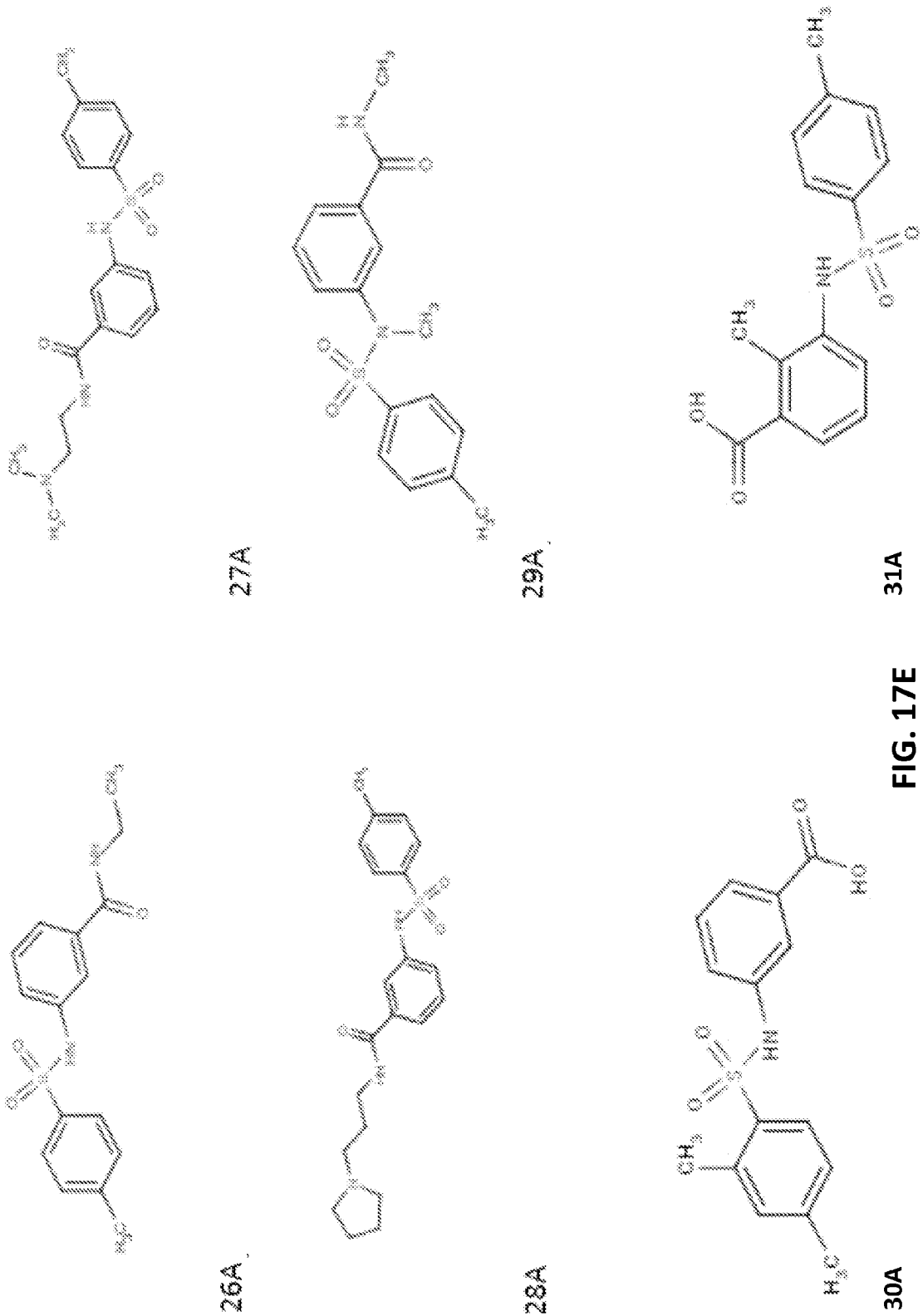
Figure 17F:
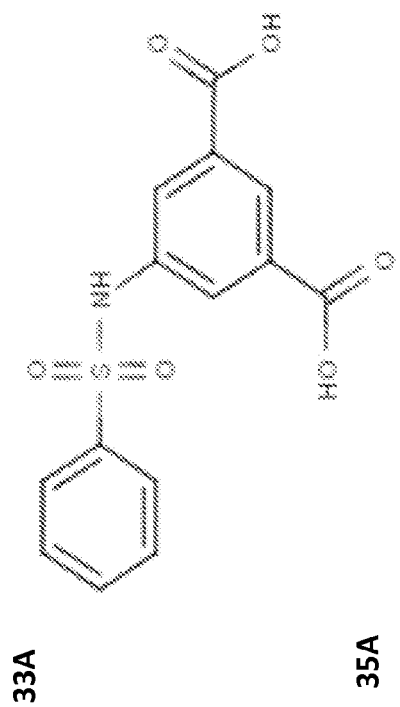
Figure 17F:
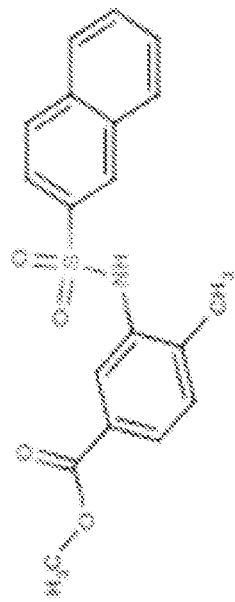
Figure 17F:
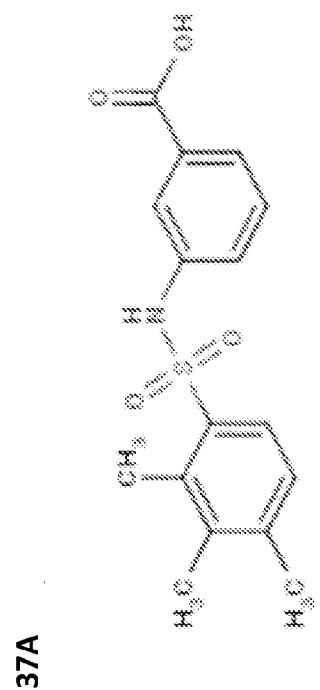
Figure 17F:
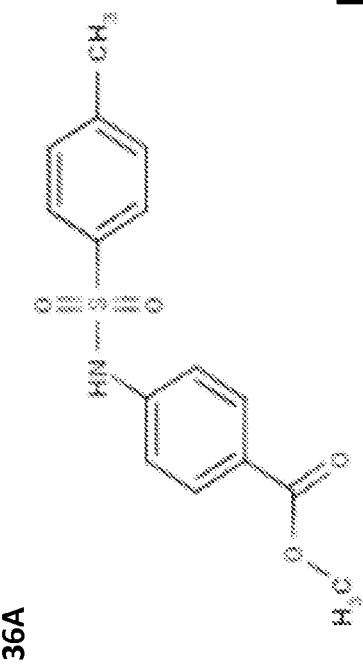
Figure 17G:
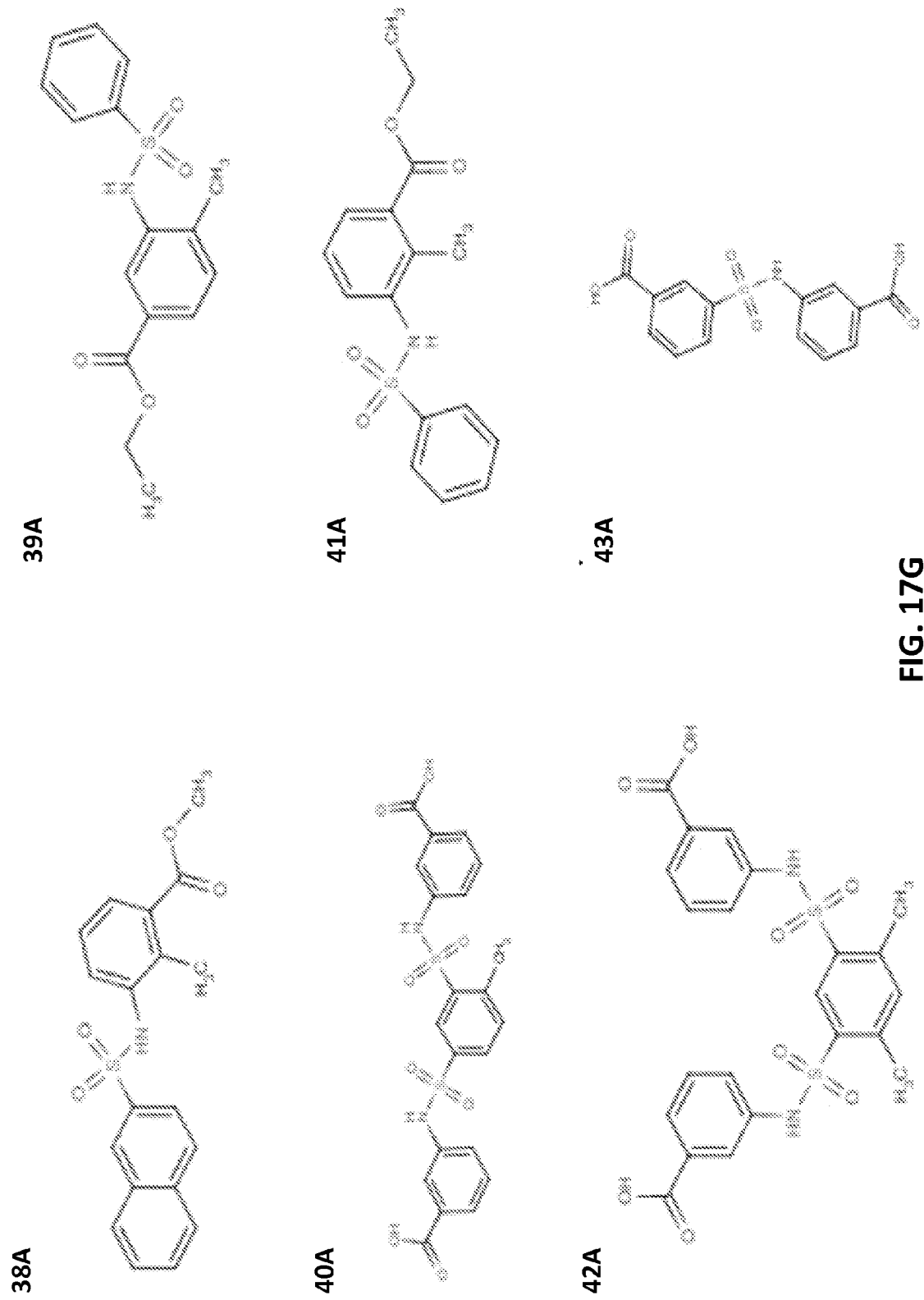
Figure 17H:
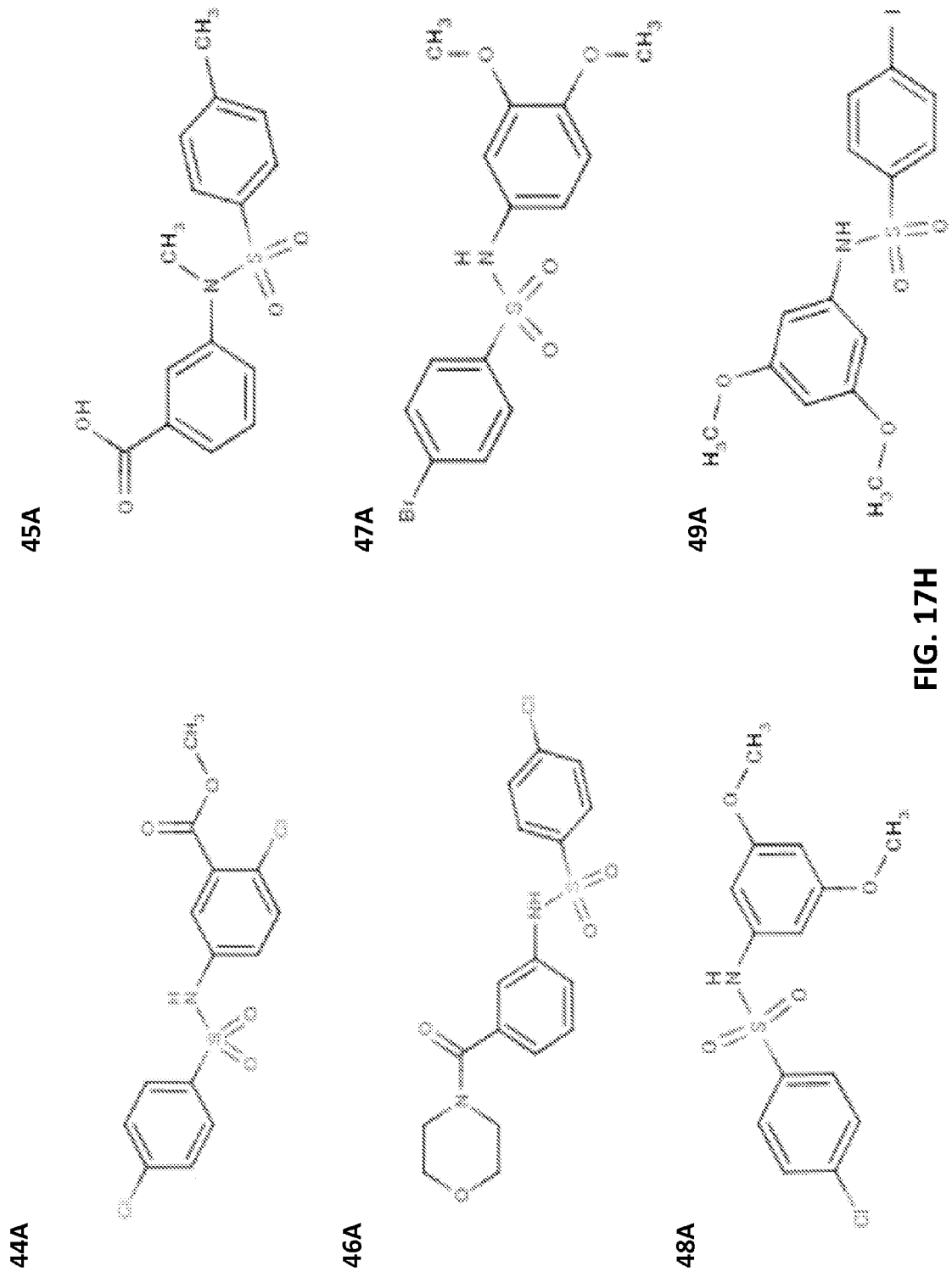
Figure 17I:
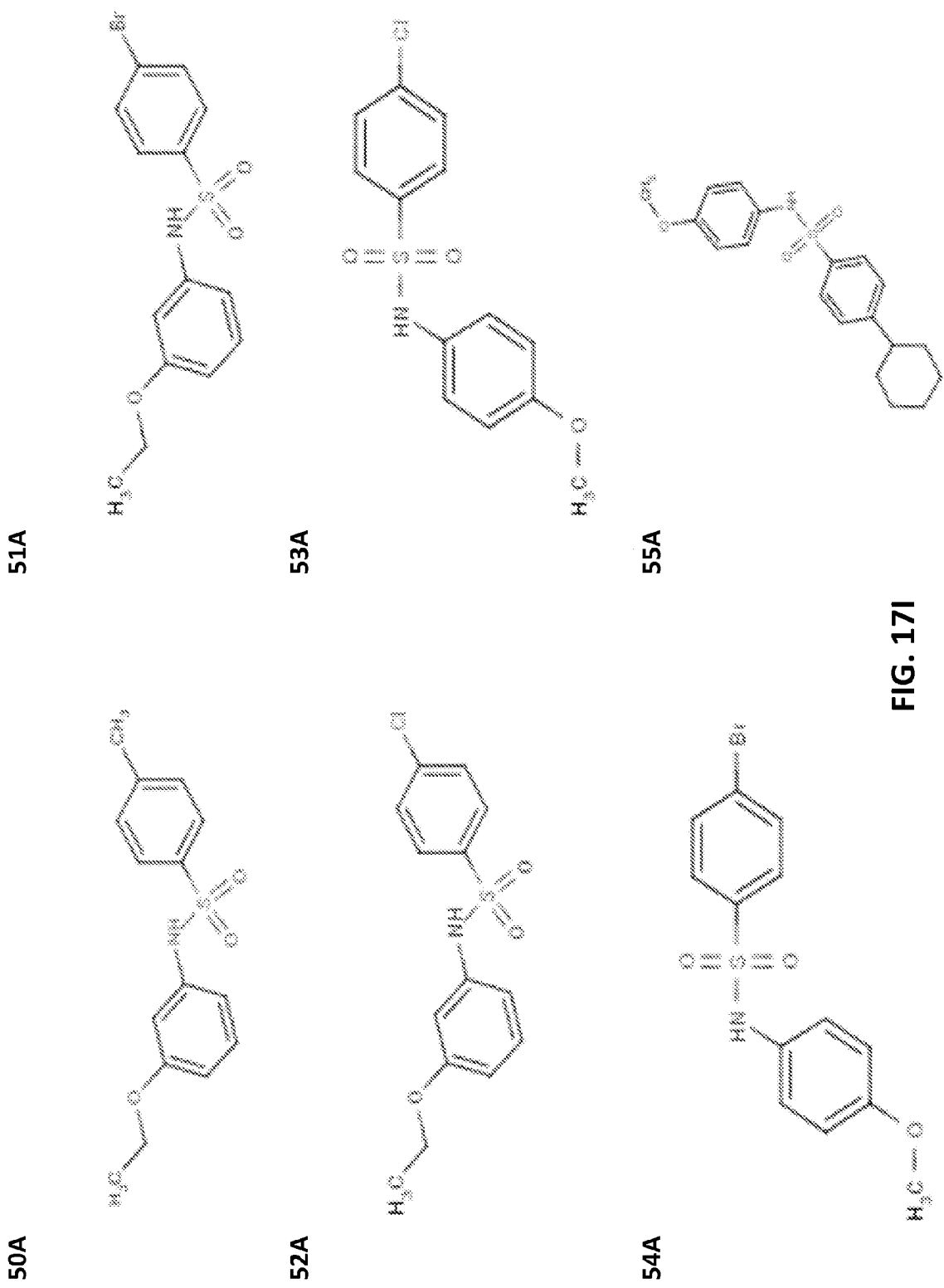

While evaluating the compounds provided herein, a number of compounds tested were found to exhibit activity levels in the assays which rendered the compounds ineffective in the methods provided herein (e.g., as inhibitors of a Wnt protein or in the treatment of cancer). For example, a compound was designated as ineffective based on the inhibition of the TCF/LEF reporter in percent of less than about 60%. Examples of such compounds are shown in FIG. 17.

E. KITS

Also provided herein are kits. Typically, a kit includes one or more compounds or compositions as described herein. In certain embodiments, a kit can include one or more delivery systems, e.g., for delivering or administering a compound as provided above, and directions for use of the kit (e.g., instructions for treating a patient). In another embodiment, the kit can include a compound or composition as described herein and a label that indicates that the contents are to be administered to a patient with cancer. In another embodiment, the kit can include a compound or composition as described herein and a label that indicates that the contents are to be administered to a patient with one or more of colorectal cancer, gastric carcinoma, hepatocellular carcinoma, fibromatosis, melanoma, medulloblastoma, and prostate cancer.

EXAMPLES

The invention is further described in the following examples, which do not limit the scope of the invention described in the claims.

Figure 2:
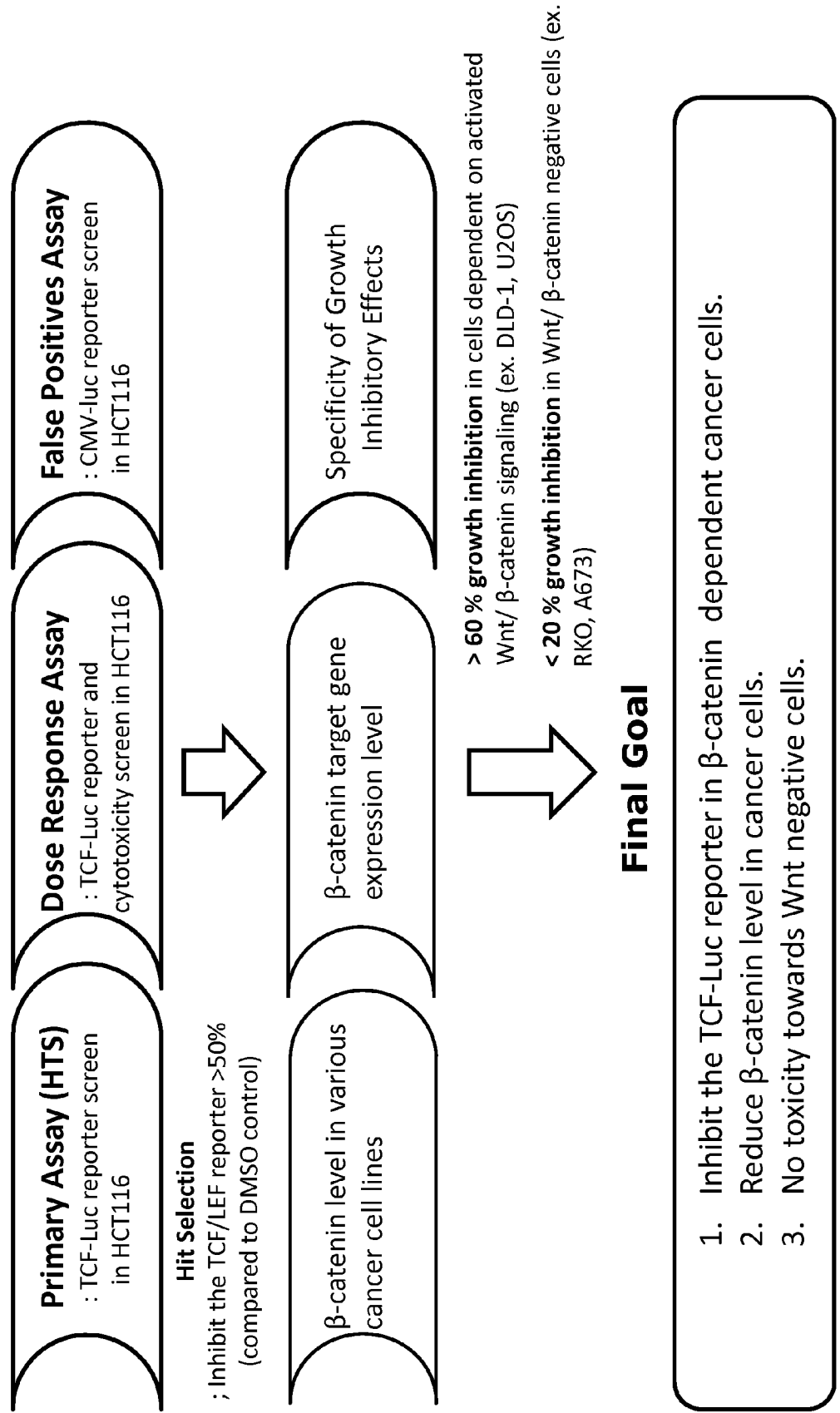
FIG. 2 shows an overview of the validation of candidates from screening.
Figure 3:
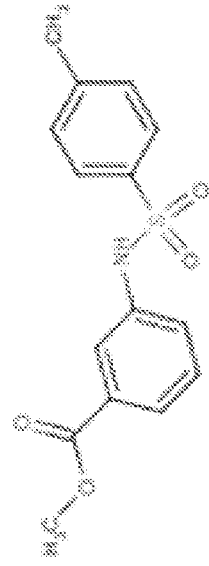
FIG. 3 shows the identification of a small molecule inhibitor/antagonist (OC0021) of the Wntbeta-catenin signaling pathway, and chemical structure, methyl 3-{[(4-methylphenyl)sulfonyl]amino}benzoate, which inhibits the TCF/LEF reporter activity.
Figure 3:
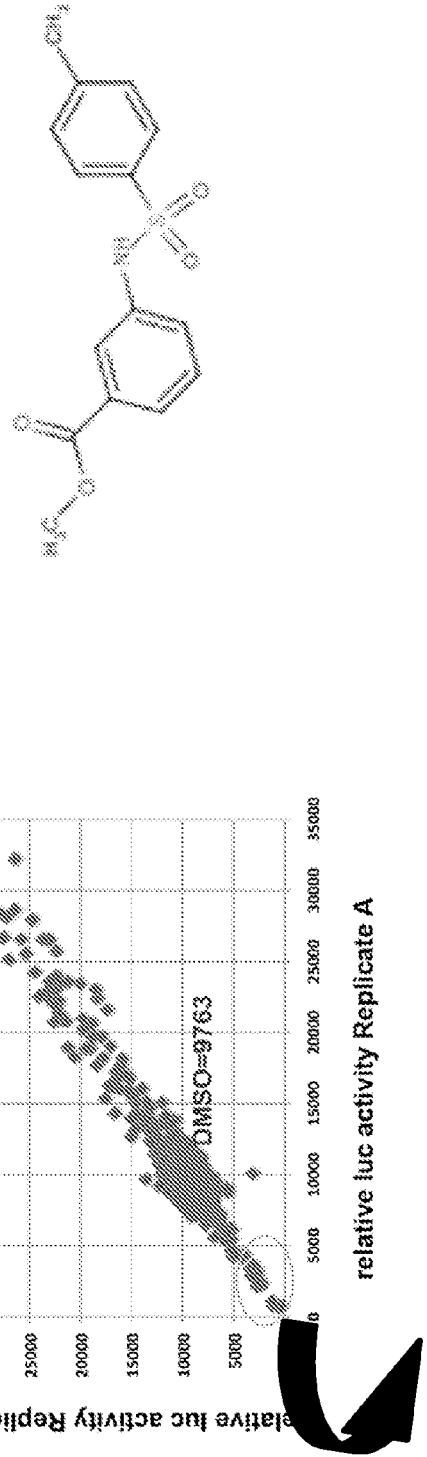
Figure 4:
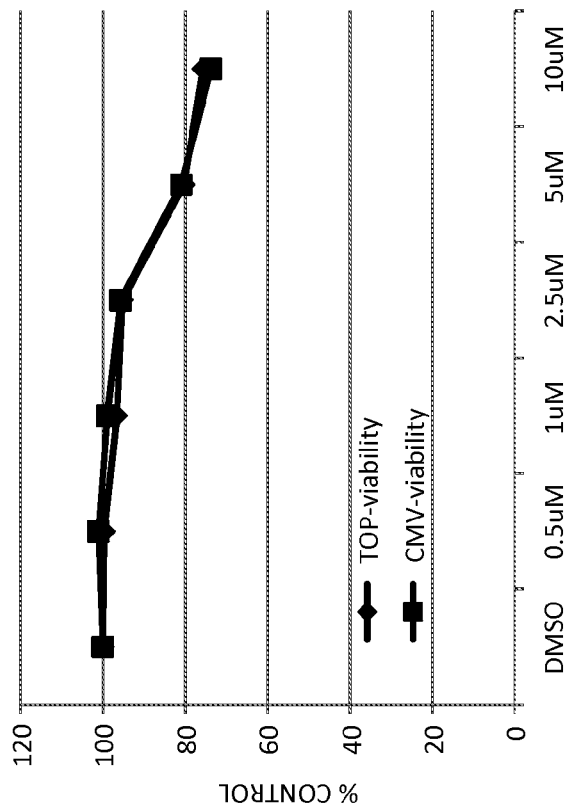
FIG. 4 shows that compound OC0021 inhibits the transcriptional activity of β-catenin/TCF in a dose dependent manner in human colon cancer cells HCT116 with beta-catenin mutation.
Figure 4:
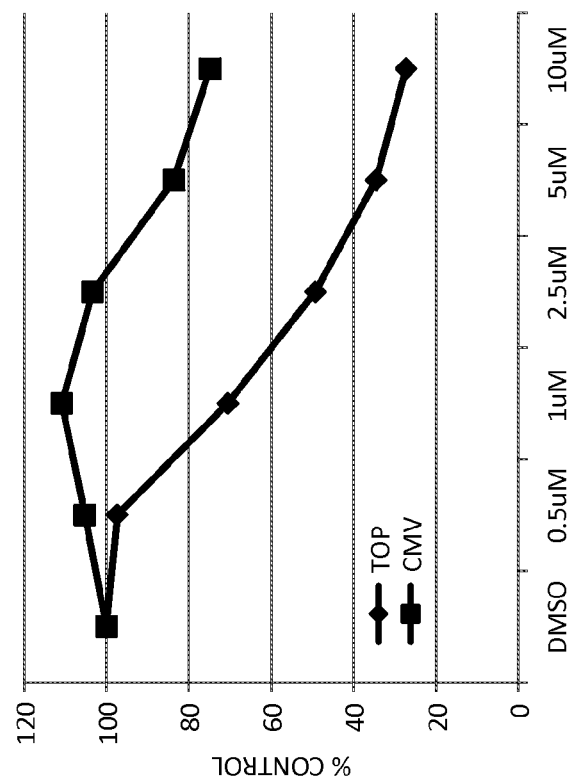
Figure 5:
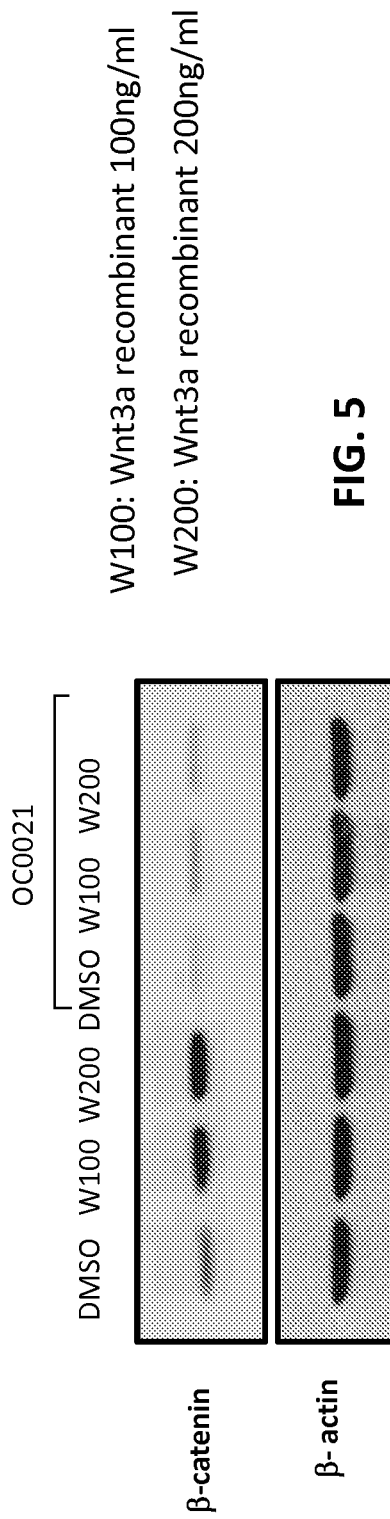
FIG. 5 shows that OC0021 inhibits Wnt-induced β-catenin accumulation.
Figure 6:
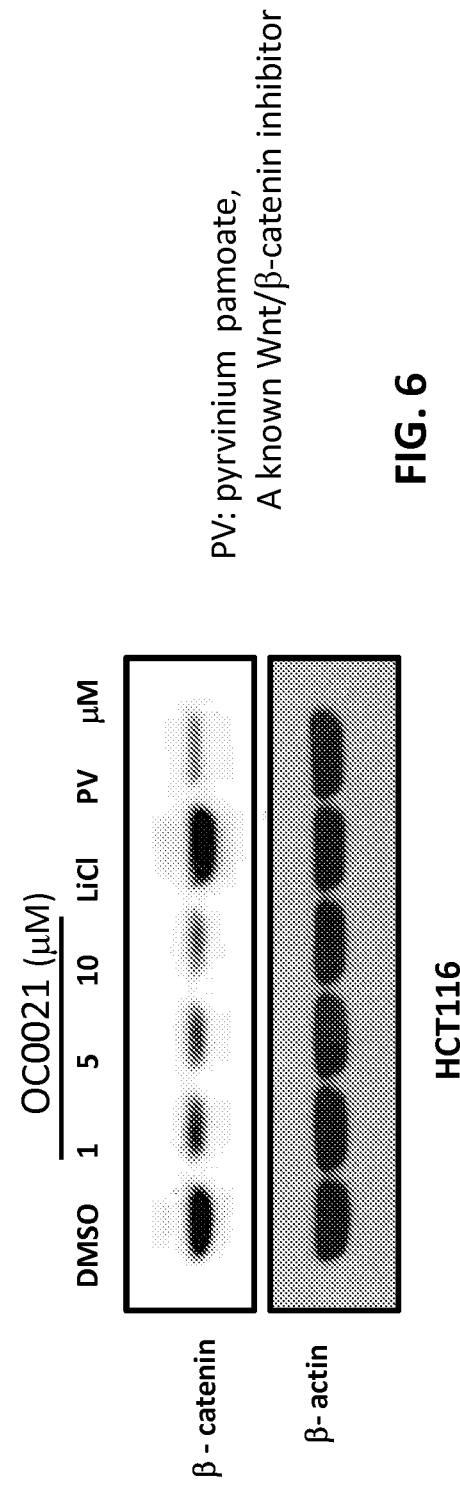
FIG. 6 shows OC0021 treatment decreases beta-catenin protein levels in HCT116 cells.
Figure 7:
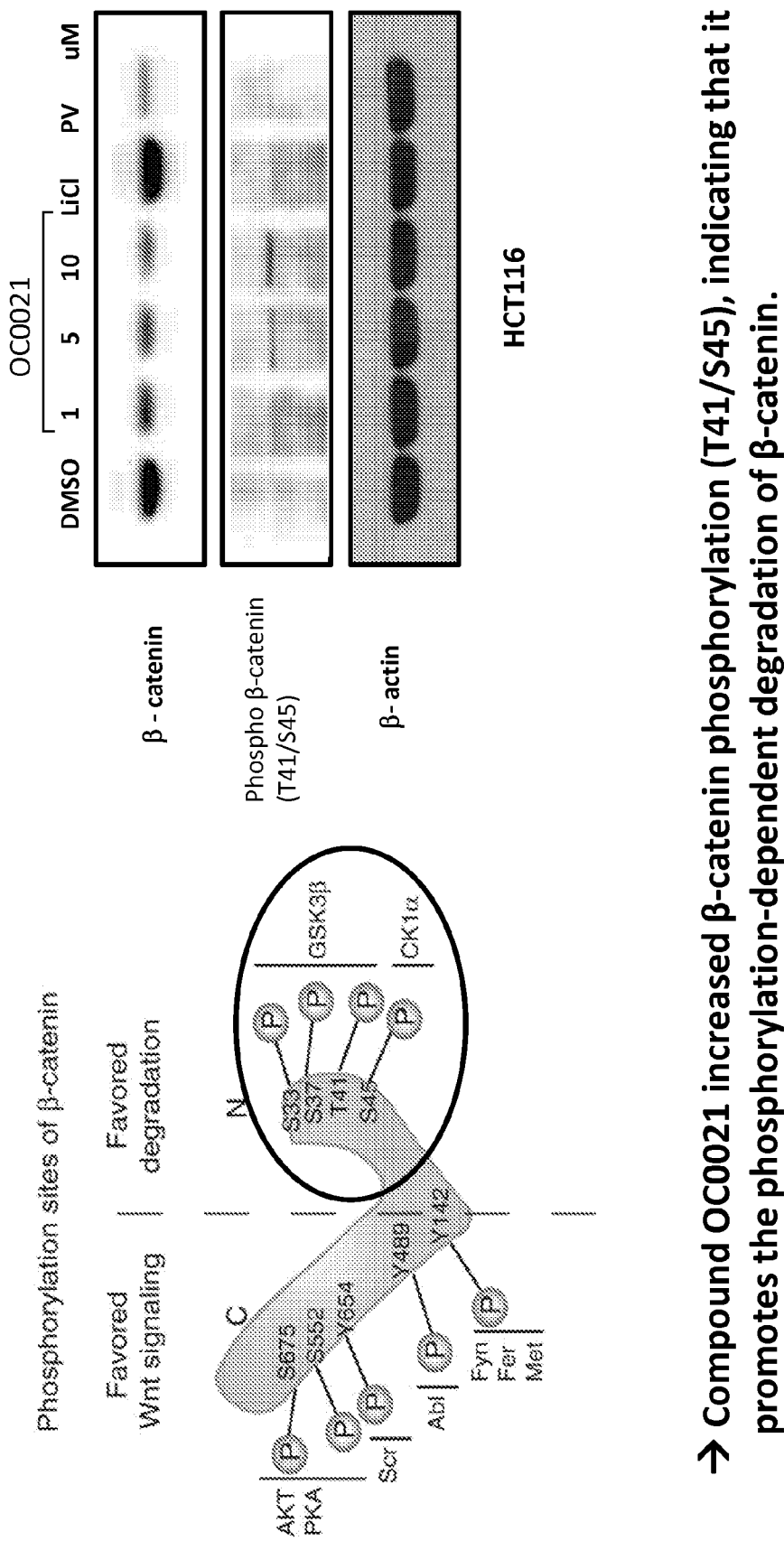
FIG. 7. Shows that OC0021 promotes β-catenin degradation via increased β-catenin phosphorylation at T41/S45 in HCT116 colon cancer cells.
Figure 8A:
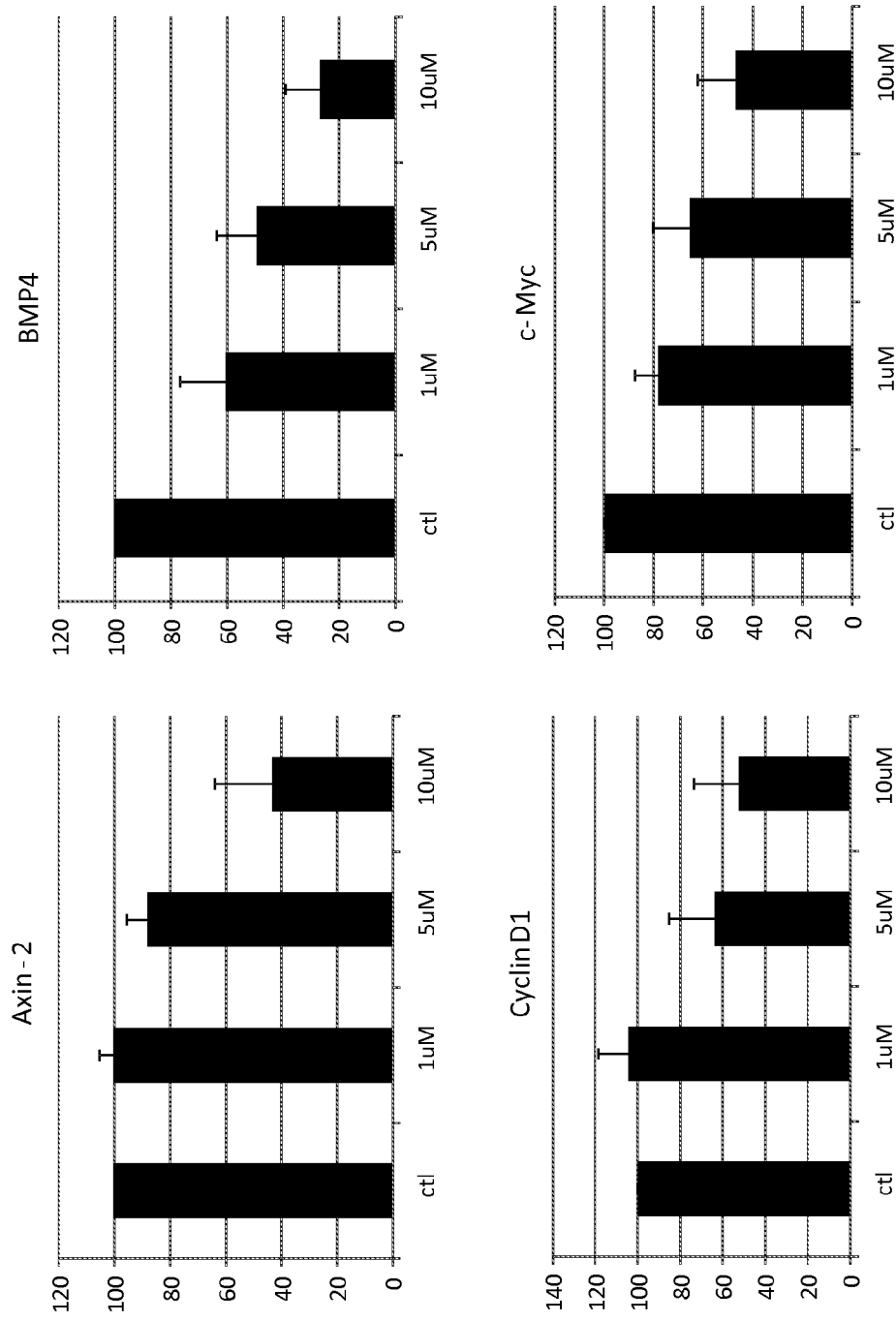
FIG. 8 shows that OC0021 modulates Wnt/β-catenin-mediated gene transcription, especially oncogenic targets such as Myc, cyclin D1, and Axin1 and 2. A. mRNA expression was measured by Real-time quantitative PCR. B. Compound OC0021 down regulates the protein level of endogenous β-catenin/TCF-dependent genes, Cyclin D1 and c-Myc, and enhances stability of Axin1 and Axin2.
Figure 8B:
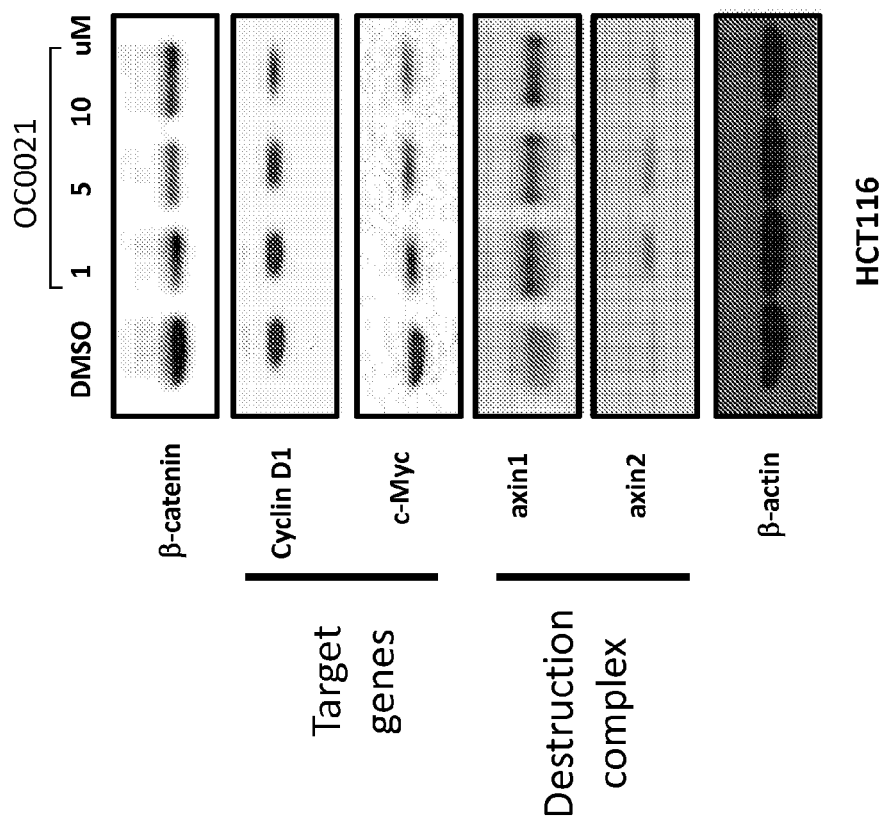
Figure 9:
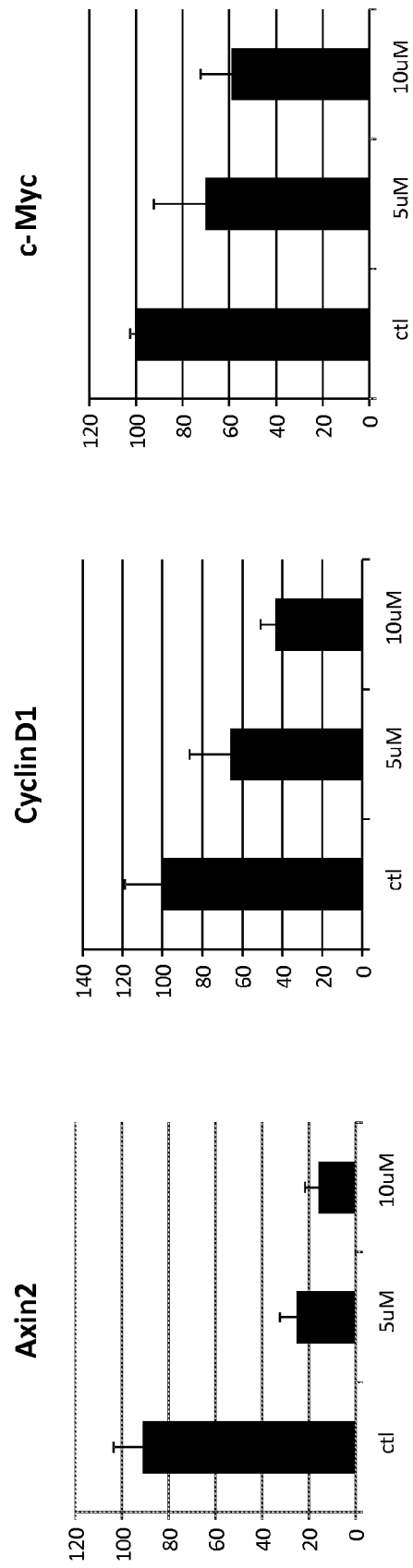
FIG. 9 shows that the effect of OC0021 on the recruitment of β-catenin to its target promoters: Compound OC0021 treatment in HCT116 cells inhibits beta-catenin binding its target gene promoters measured by ChIP-RT-PCR (Chromatin-Immunoprecipation followed by Quantitative real-time PCR) experiments.
Figure 10:
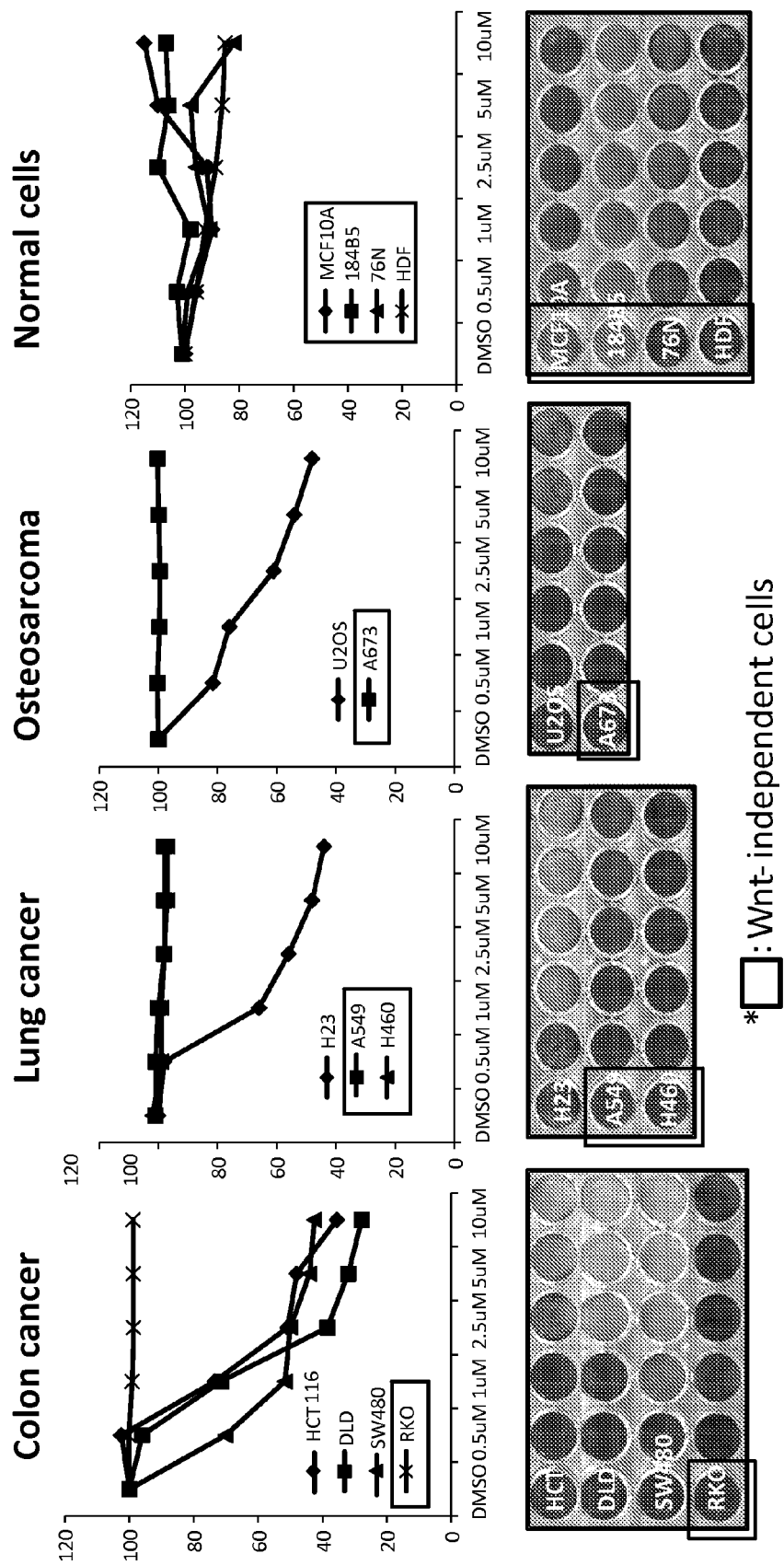
FIG. 10 shows the cytotoxic effect of OC0021 on Wnt/β-catenin-dependent cancer cells but no significant cytotoxic in Wnt/β-catenin-independent cancer cells as well as in normal cells.
Figure 11:
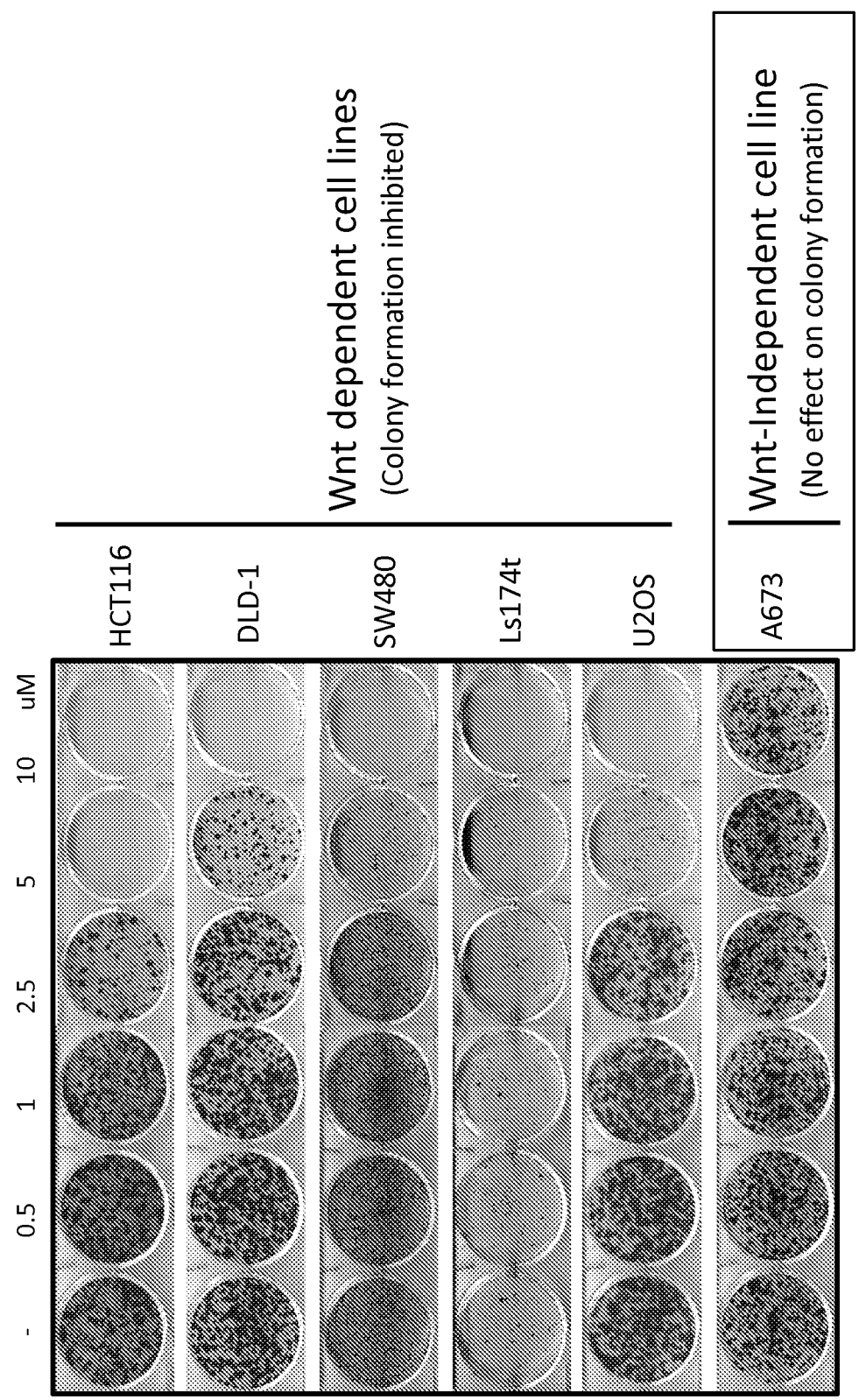
FIG. 11 shows that OC0021 inhibits colony formation in a number of Wnt/β-catenin-dependent cancer cells in a dose-dependent manner.
Figure 12:
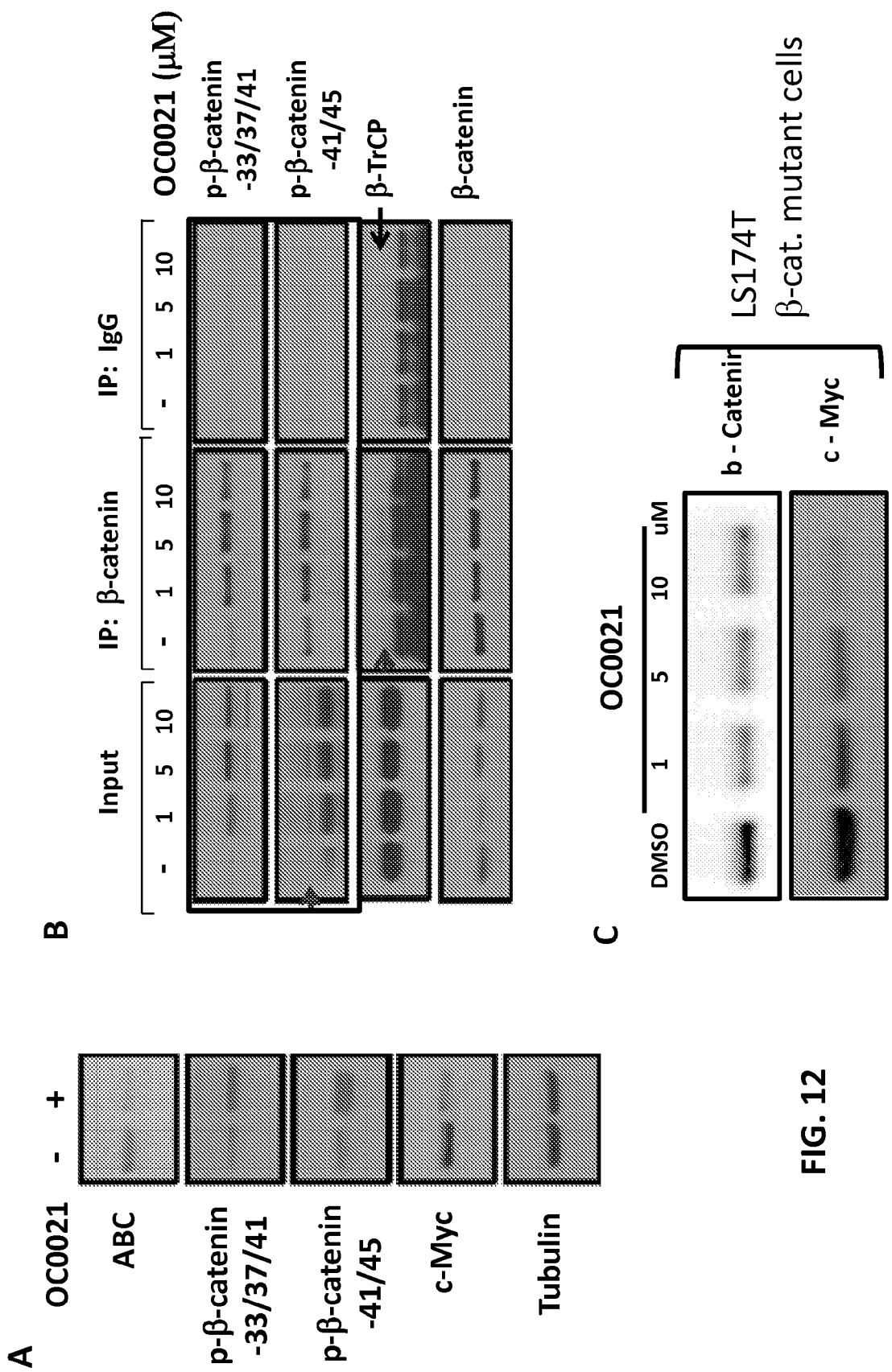
FIG. 12 shows that OC0021-mediated beta-catenin degradation results from an increase of β-catenin phosphorylation, which represents the mechanism of action for OC0021. OC0021 treatment supresses ABC (Active form of b-catenin) but increases phosphorylated β-catenins (phospho-β-catenin-33/37/41; -41/45), and also inhibits the expression of oncogene Myc target gene (A-C, performed by Western blotting and Immunoprecipitation experiments).
Figure 13A:
FIG. 13 shows the anti-tumor activity of OC0021 in Wnt/β-catenin-dependent colon tumors in mice (xenograft studies). A, HCT116 colon cancer cells; B, HT115 colon cancer cells; and C, H23 human lung cancer cells. 20 mg/kg was injected daily via i.p.
Figure 13A:
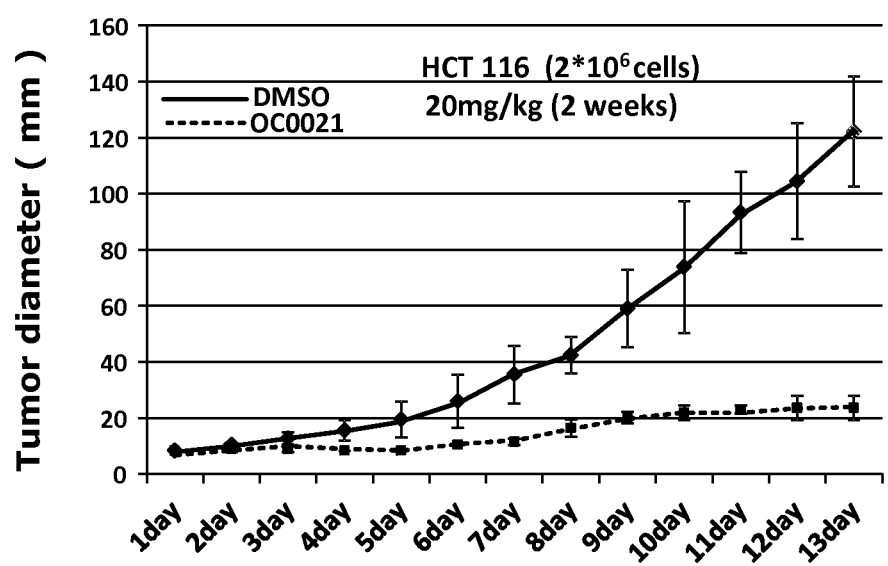
Figure 13B:
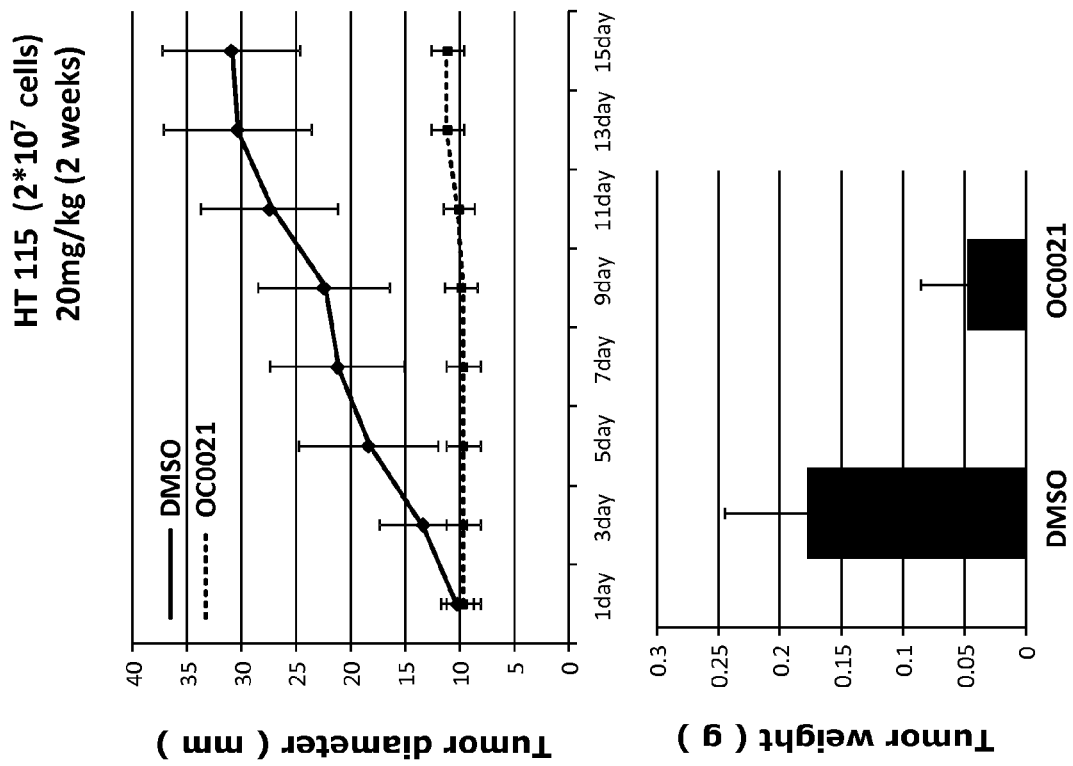
Figure 13B:
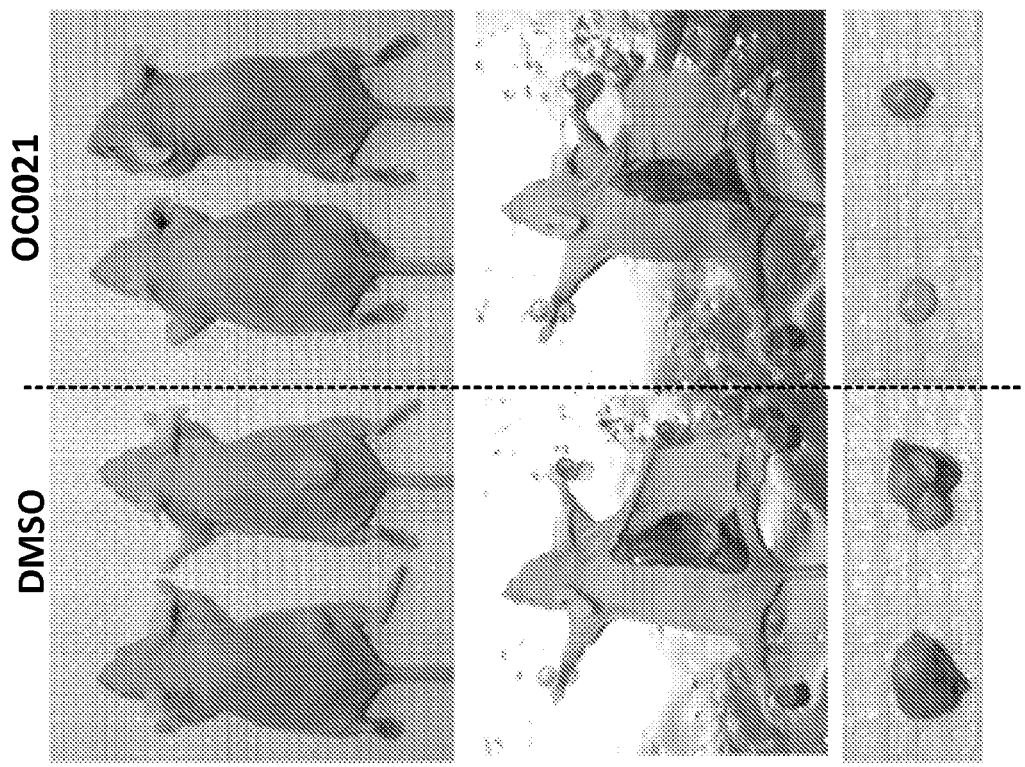
Figure 13C:
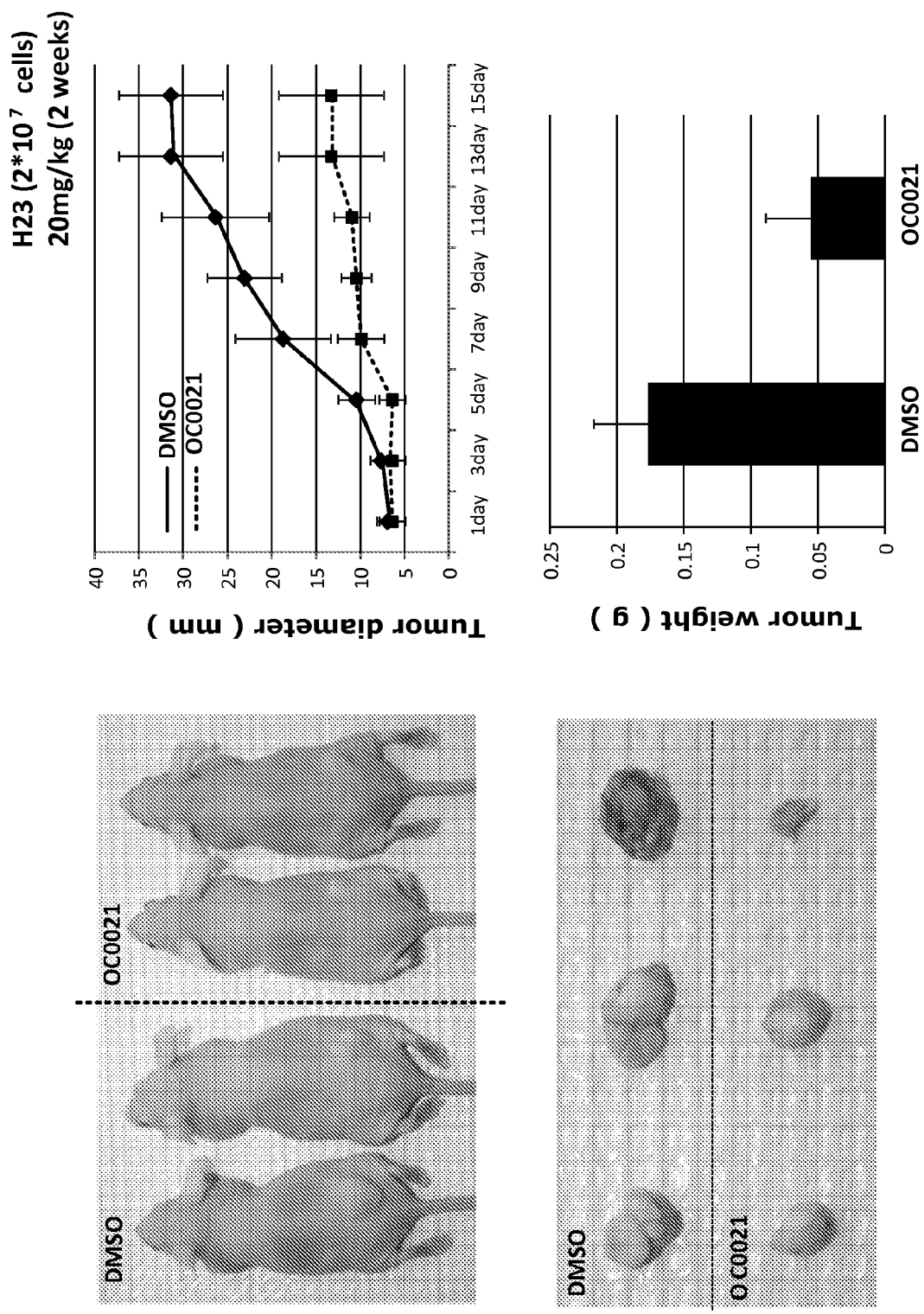
Figure 14:
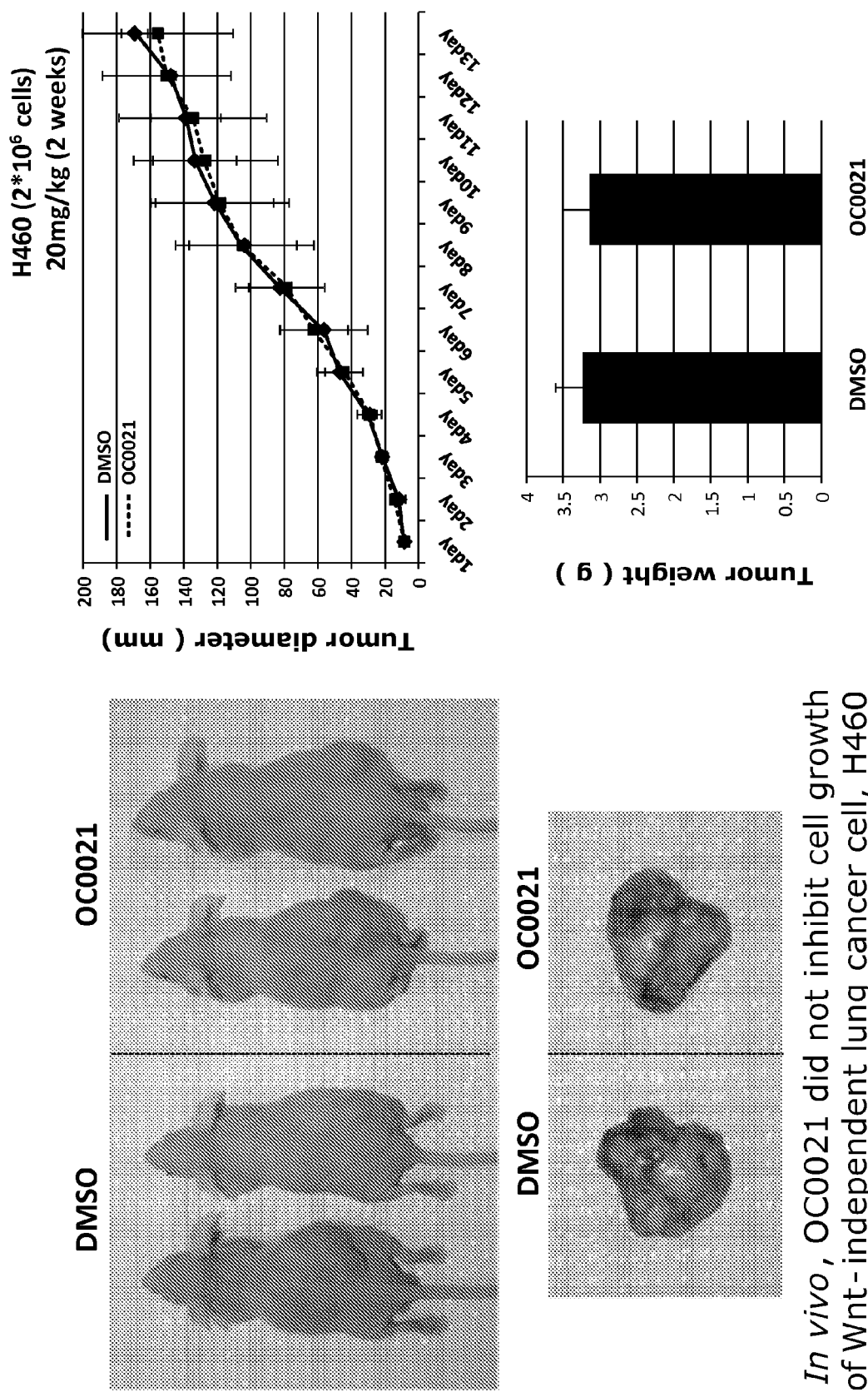
FIG. 14 shows that OC0021 does not affect Wnt/b-catenin-independent tumor growth in mice (H460 human lung cancer cells).
Figure 15:
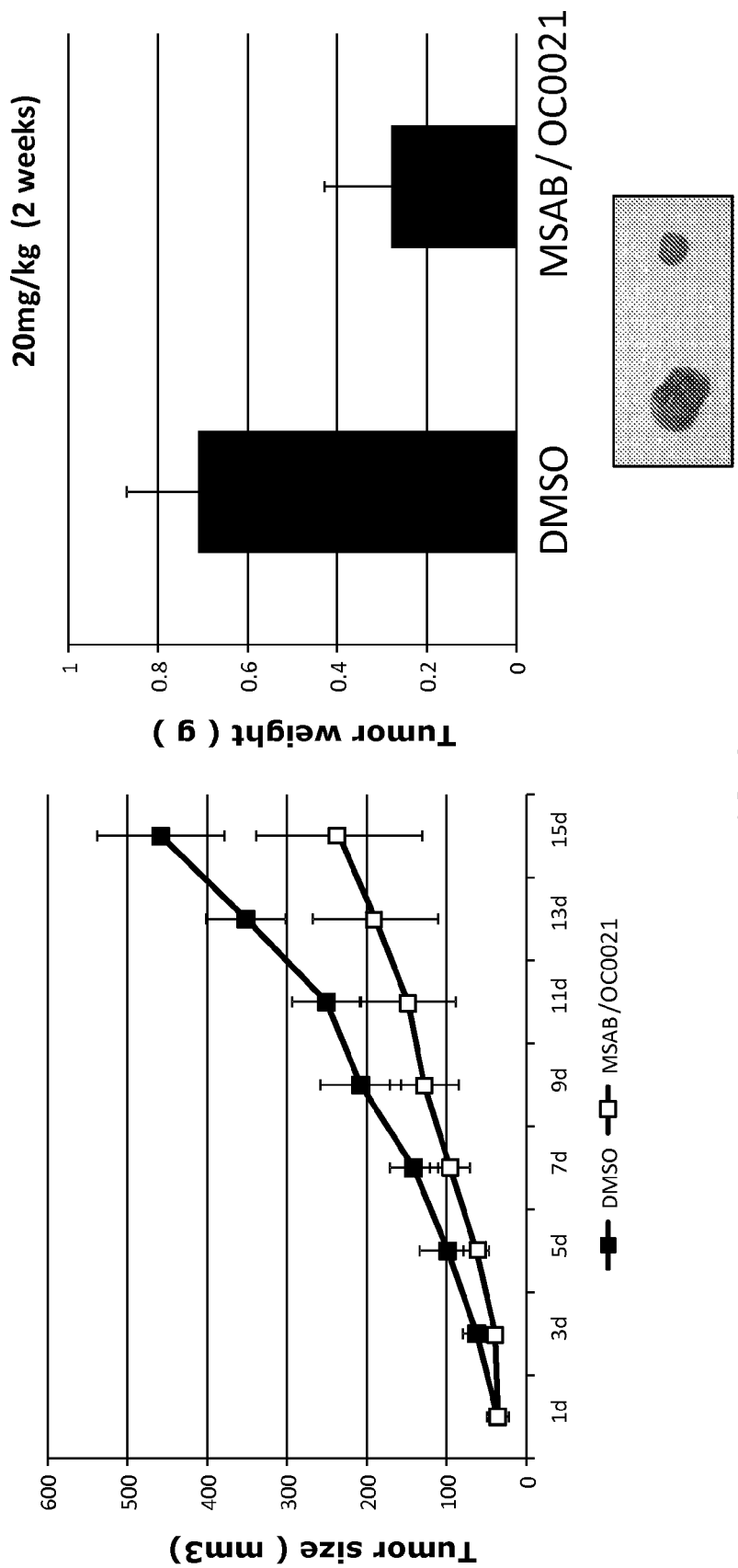
FIG. 15 shows that OC0021 inhibits the growth of mammary tumor in a spontaneous mouse model of breast cancer (MMTV-Wnt1 tumor mice).
Figure 16A:
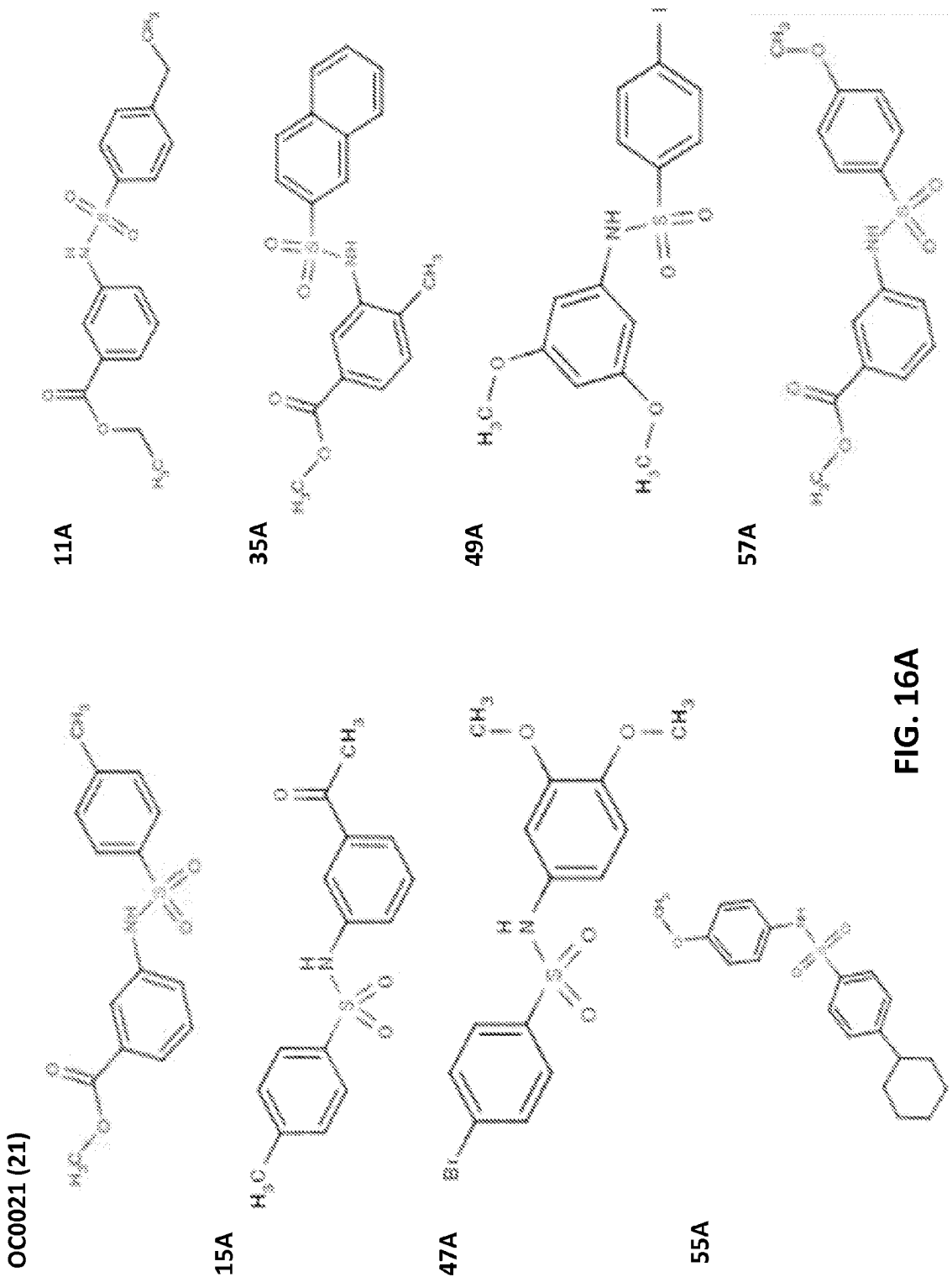
FIG. 16 shows the compounds provided for the methods described herein.
Figure 16B:
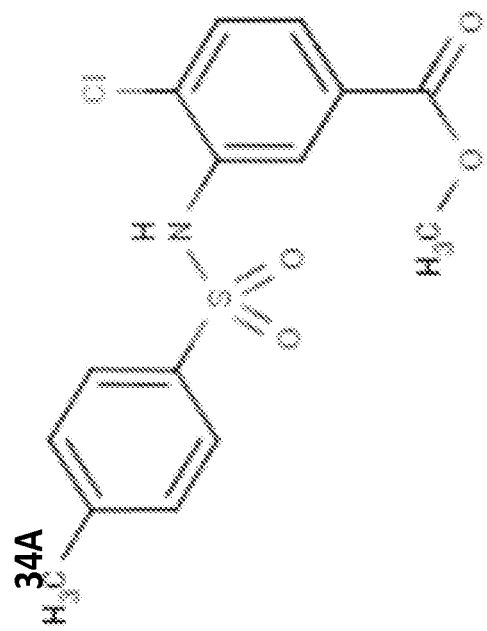
Figure 16B:
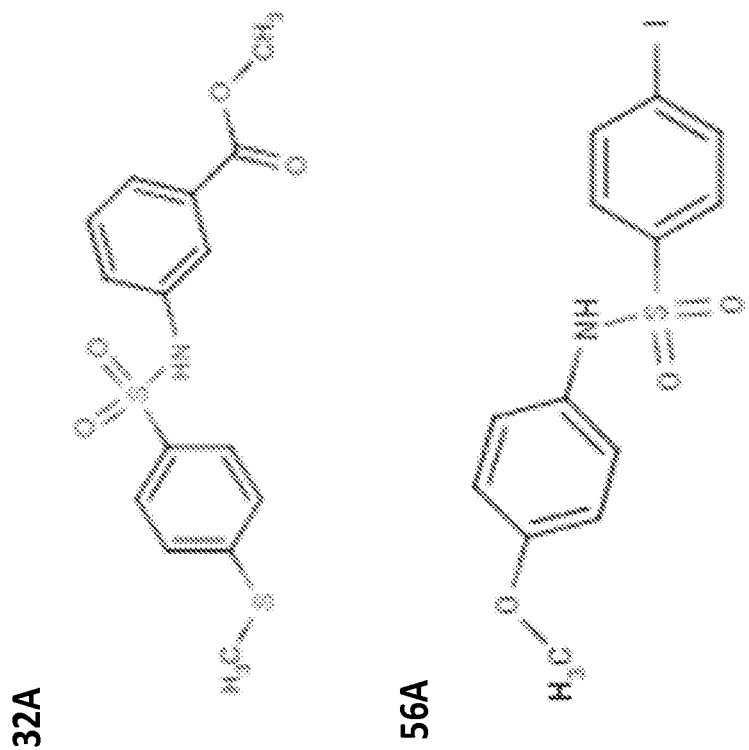
Figure 18A:
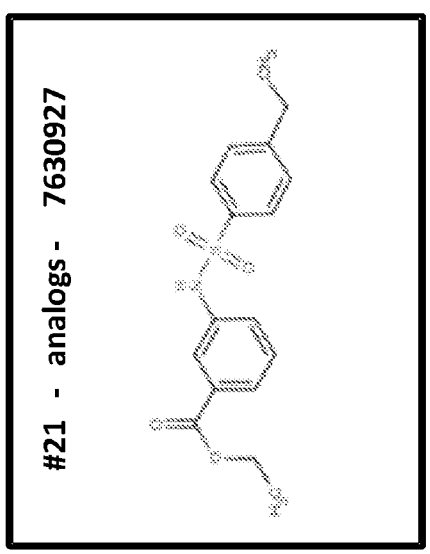
FIG. 18 shows testing of analogs of the lead compound (21) for inhibitory activity of the Wnt/beta-catenin signaling pathway. "Top" shows assay for inhibition of the TCF/LEF reporter activity; "CMV" is a non-specific reporter gene activity: "TOP-SRB" is cell death in the cells with TCF/LEF reporter: "CMV-SRB" shows cell death in the cells with non-specific reporter.
Figure 18A:
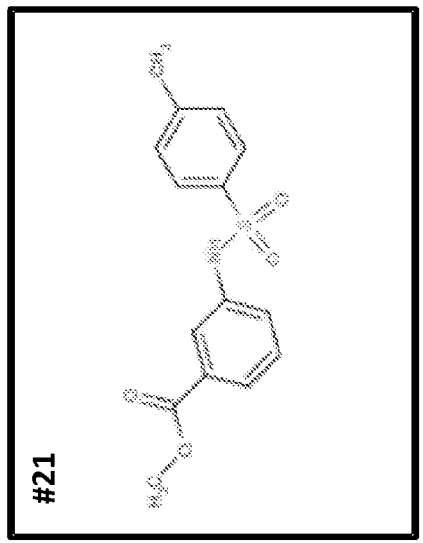
Figure 18A:
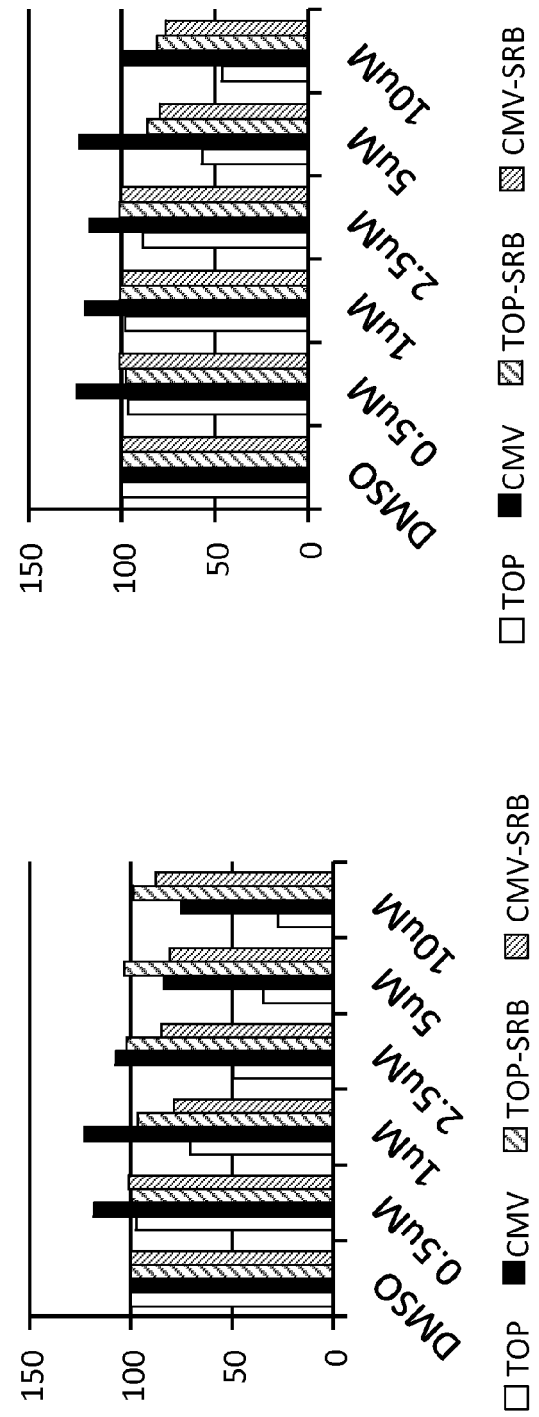
Figure 18B:
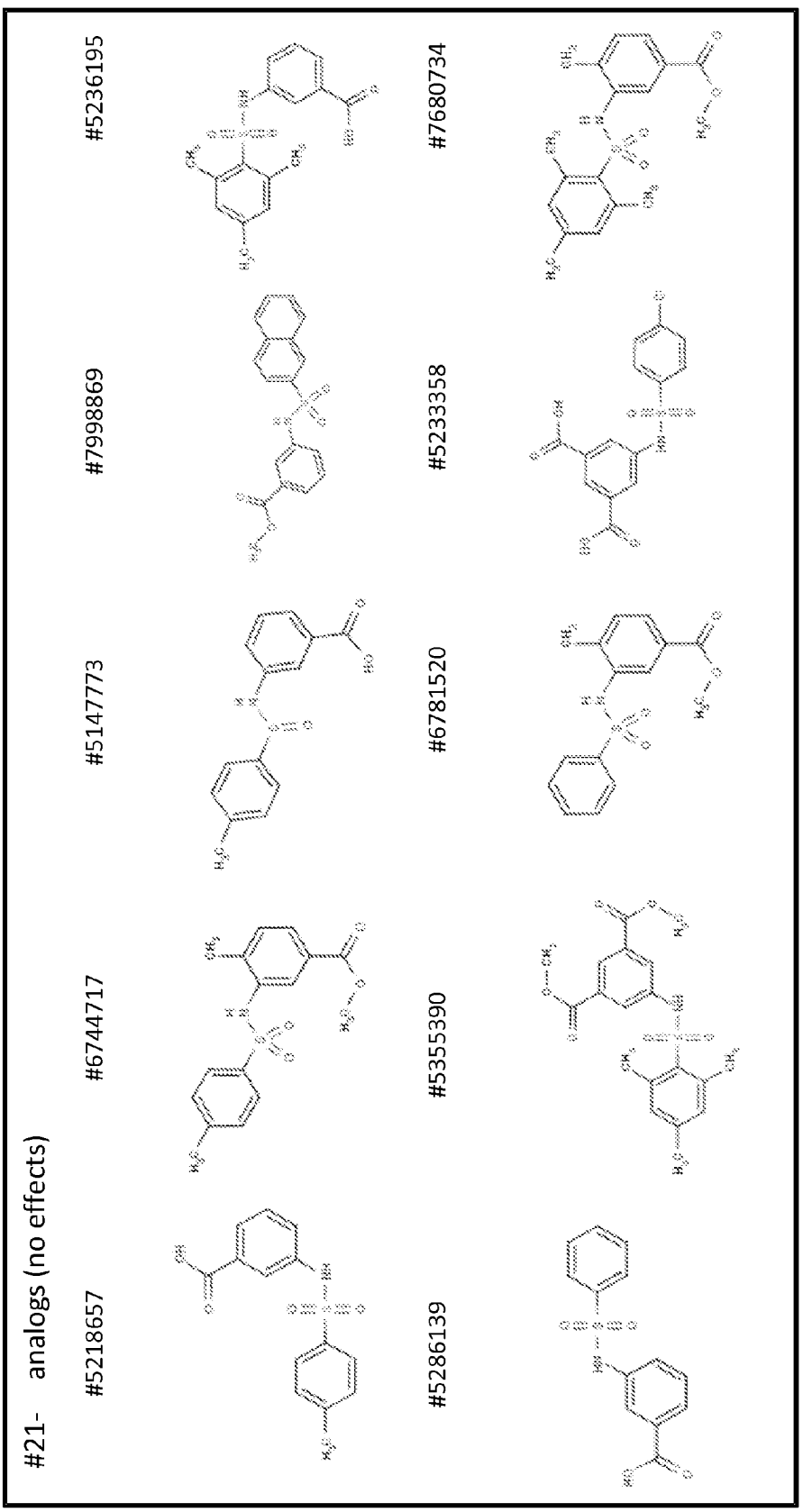

The data displayed in FIGS. 1-18 were obtained using known literature procedures. See, for example:

Polakis P. Drugging Wnt signalling in cancer. *EMBO J.* 2012 May 22; 31(12):2737-46; Bialkowska A B, Yang V W. High-throughput screening strategies for targeted identification of therapeutic compounds in colorectal cancer. *Future Oncol.* 2012 March; 8(3):259-72;

Huang S M, Mishina Y M, Liu S, Cheung A, Stegmeier F, Michaud G A, Charlat O, Wiellette E, Zhang Y, Wiessner S. Hild M, Shi X, Wilson C J, Mickanin C. Myer V, Fazal A, Tomlinson R, Serluca F, Shao W, Cheng H, Shultz M, Rau C, Schirle M, Schlegl J, Ghidelli S, Fawell S, Lu C, Curtis D, Kirschner M W, Lengauer C. Finan P M, Tallarico J A, Bouwmeester T, Porter J A, Bauer A, Cong F. Tankyrase inhibition stabilizes axin and antagonizes Wnt signalling. *Nature.* 2009 Oct. 1; 461(7264):614-20;

Chen B, Dodge M E, Tang W, Lu J, Ma Z, Fan C W, Wei S, Hao W, Kilgore J, Williams N S, Roth M G, Amatruda J F. Chen C. Lum L. Small molecule-mediated disruption of Wnt-dependent signaling in tissue regeneration and cancer. *Nat Chem. Biol.* 2009 February; 5(2): 100-7;

Thorne C A, Hanson A J, Schneider J, Tahinci E, Orton D, Cselenyi C S, Jernigan K K, Meyers K C, Hang B I, Waterson A G, Kim K, Melancon B, Ghidu V P, Sulikowski G A, LaFleur B, Salic A, Lee L A, Miller D M 3rd, Lee E. Small-molecule inhibition of Wnt signaling through activation of casein kinase 1α. *Nat Chem. Biol.* 2010 November; 6(11):829-36;

Wei W, Chua M S. Grepper S, So S. Small molecule antagonists of Tcf4/beta-catenin complex inhibit the growth of HCC cells in vitro and in vivo. *Int J Cancer.* 2010 May 15; 126(10):2426-36;

Lepourcelet M, Chen Y N, France D S, Wang H, Crews P, Petersen F, Bruseo C, Wood A W, Shivdasani R A. Small-molecule antagonists of the oncogenic Tcf/beta-catenin protein complex. *Cancer Cell.* 2004 January; 5(1):91-102;

Grossmann T N, Yeh J T, Bowman B R, Chu Q, Moellering R E, Verdine G L. Inhibition of oncogenic Wnt signaling through direct targeting of β-catenin. *Proc Natl Acad Sci USA.* 2012 Oct. 15. [in press];

Bafico A. Gazit A, Wu-Morgan S S, Yaniv A, Aaronson S A. Characterization of Wnt-1 and Wnt-2 induced growth alterations and signaling pathways in NIH3T3 fibroblasts. *Oncogene.* 1998 May 28; 16(21):2819-25;

Ewan K, Pajak B, Stubbs M, Todd H, Barbeau O, Quevedo C, Botfield H, Young R, Ruddle R, Samuel L, Battersby A. Raynaud F, Allen N, Wilson S, Latinkic B, Workman P, McDonald E, Blagg J, Aherne W, Dale T. A useful approach to identify novel small-molecule inhibitors of Wnt-dependent transcription. *Cancer Res.* 2010 Jul. 15; 70(14):5963-73;

Bafico A, Liu G, Goldin L, Harris V, Aaronson S A. An autocrine mechanism for constitutive Wnt pathway activation in human cancer cells. *Cancer Cell.* 2004 November; 6(5):497-506;

Chen H J, Hsu L S, Shia Y T, Lin M W, Lin C M. The β-catenin/TCF complex as a novel target of resveratrol in the Wnt/β-catenin signaling pathway. *Biochem Pharmacol.* 2012 Nov. 1; 84(9):1143-53;

Barker N, Clevers H. Mining the Wnt pathway for cancer therapeutics. *Nat Rev Drug Discov.* 2006 December; 5(12):997-1014;

Clevers H, Nusse R. Wnt/β-catenin signaling and disease. *Cell.* 2012 Jun. 8; 149(6):1192-205;

Xie J, Xiang D B, Wang H, Zhao C, Chen J, Xiong F, Li T Y, Wang X L. Inhibition of tcf-4 induces apoptosis and enhances chemosensitivity of colon cancer cells. *PLoS One.* 2012; 7(9):e45617;

Akiri G, Cheman M M, Vijayakumar S, Liu G, Bafico A, Aaronson S A. Wnt pathway aberrations including autocrine Wnt activation occur at high frequency in human non-small-cell lung carcinoma. *Oncogene.* 2009 May 28; 28(21):2163-72;

Liu X H, Kirschenbaum A, Yao S, Liu G, Aaronson S A, Levine A C. Androgen-induced Wnt signaling in preosteoblasts promotes the growth of MDA-PCa-2b human prostate cancer cells. *Cancer Res.* 2007 Jun. 15; 67(12):5747-53;

Song S, Christova T, Perusini S, Alizadeh S, Bao R Y, Miller B W, Hurren R. Jitkova Y, Gronda M, Isaac M, Joseph B, Subramaniam R, Aman A, Chau A, Hogge D E, Weir S J, Kasper J, Schimmer A D, Al-awar R, Wrana J L, Attisano L. Wnt inhibitor screen reveals iron dependence of β-catenin signaling in cancers. *Cancer Res.* 2011 Dec. 15; 71(24):7628-39.

Raj L, Ide T, Gurkar A U, Foley M, Schenone M, Li X, Tolliday N J, Golub T R, Carr S A, Shamji A F, Stern A M, Mandinova A, Schreiber S L, Lee S W. Selective killing of cancer cells by a small molecule targeting the stress response to ROS. *Nature.* 2011 Jul. 13; 475(7355):231-4;

Huang S, Li Y, Chen Y, Podsypanina K, Chamorro M, Olshen A B, Desai K V, Tann A, Petersen D, Green J E, Varmus H E. Changes in gene expression during the development of mammary tumors in MMTV-Wnt-1 transgenic mice. *Genome Biol.* 2005; 6(10):R84.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating cancer in a patient, the method comprising administering to the patient a therapeutically effective amount of a compound selected from the group consisting of:

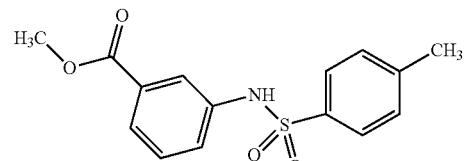

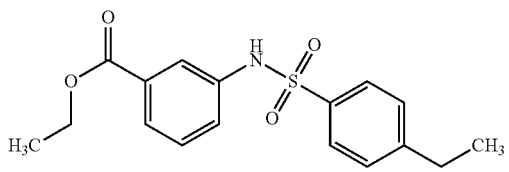

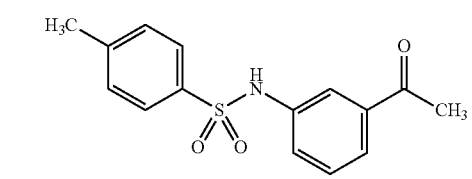

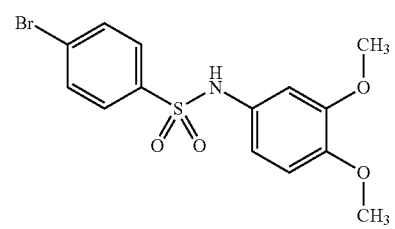

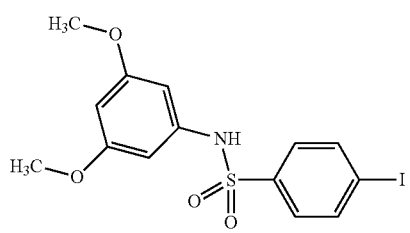

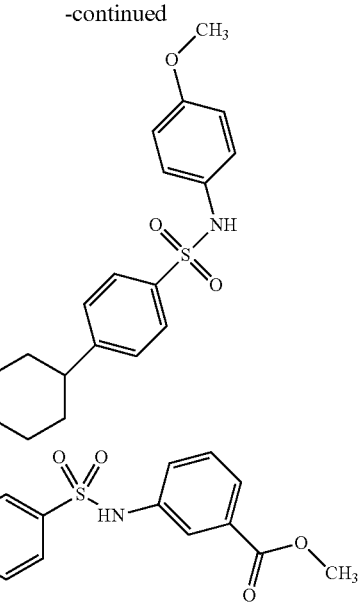

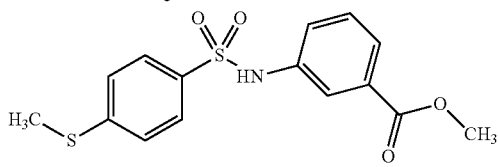

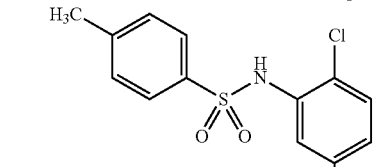

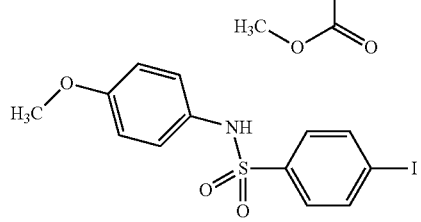

or a pharmaceutically acceptable salt thereof.

2. The method of claim 1, wherein the compound is:

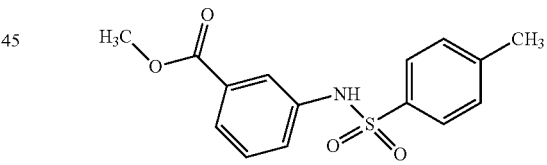

or a pharmaceutically acceptable salt thereof.

3. The method of claim 1, wherein the patient is a human.

4. The method of claim 1, wherein the cancer is selected from the group consisting of: colorectal cancer, gastric carcinoma, heptaocellulcar carcinoma, fibromatosis, melanoma, medulloblastoma, and prostate cancer.

5. The method of claim 1, wherein the compound inhibits one or more proteins in the Wnt pathway.

6. The method of claim 4, wherein the compound inhibits one or more Wnt proteins.

7. The method of claim 5, wherein the Wnt proteins are chosen from: WNT1, WNT2, WNT2B, WNT3, WNT3A, WNT4, WNT5A, WNT5B, WNT6, WNT7A, WNT7B, WNT8A, WNT8B, WNT9A, WNT9B, WNT10A, WNT10B, WNT11, and WNT16.

8. The method of claim 1, wherein the cancer is a Wnt-dependent cancer.

9. The method of claim 1, wherein the compound is selected from the group consisting of:
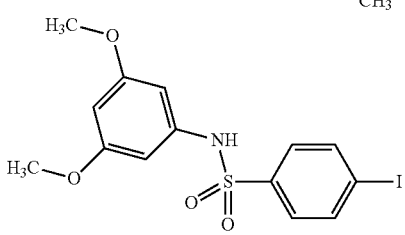
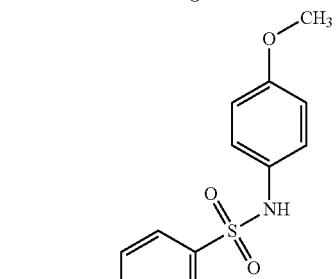
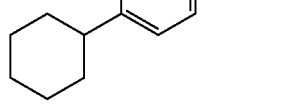
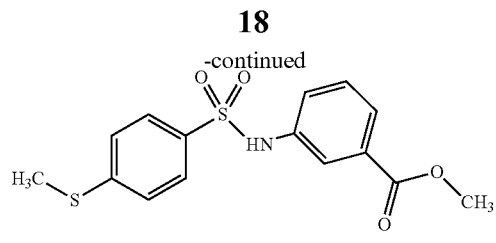
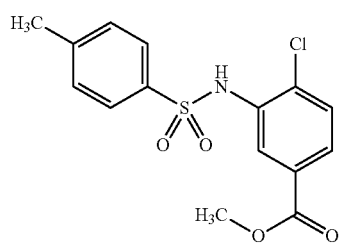
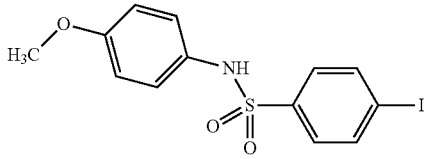
or a pharmaceutically acceptable salt thereof.
* * * * *